(12) United States Patent
Picher et al.

(10) Patent No.: US 11,299,718 B2
(45) Date of Patent: Apr. 12, 2022

(54) METHODS FOR AMPLIFICATION AND SEQUENCING USING THERMOSTABLE TTHPRIMPOL

(71) Applicant: 4basebio SL, Madrid (ES)

(72) Inventors: Angel J. Picher, Madrid (ES); Luis Blanco, Madrid (ES)

(73) Assignee: 4BASEBIO SL, Madrid (ES)

( * ) Notice: Subject to any disclaimer, the term of this patent is extended or adjusted under 35 U.S.C. 154(b) by 879 days.

(21) Appl. No.: 14/776,901

(22) PCT Filed: Mar. 14, 2014

(86) PCT No.: PCT/EP2014/055158
§ 371 (c)(1),
(2) Date: Sep. 15, 2015

(87) PCT Pub. No.: WO2014/140309
PCT Pub. Date: Sep. 18, 2014

(65) Prior Publication Data
US 2016/0040143 A1    Feb. 11, 2016

(30) Foreign Application Priority Data

Mar. 15, 2013  (EP) .................................... 13159629

(51) Int. Cl.
| | |
|---|---|
| *C12N 9/12* | (2006.01) |
| *C12N 15/10* | (2006.01) |
| *C12Q 1/686* | (2018.01) |
| *C12P 19/34* | (2006.01) |

(52) U.S. Cl.
CPC ......... *C12N 9/1252* (2013.01); *C12N 15/102* (2013.01); *C12P 19/34* (2013.01); *C12Q 1/686* (2013.01); *C12Y 207/07007* (2013.01)

(58) Field of Classification Search
None
See application file for complete search history.

(56) References Cited

U.S. PATENT DOCUMENTS

| | | | |
|---|---|---|---|
| 5,001,050 A | 3/1991 | Blanco et al. | |
| 5,656,493 A | 8/1997 | Mullis et al. | |
| 2011/0294167 A1* | 12/2011 | McEwan ............... | C12Q 1/6844 435/91.2 |

FOREIGN PATENT DOCUMENTS

| | | |
|---|---|---|
| WO | WO 2011/000997 A1 | 1/2011 |
| WO | WO 2011/098588 A1 | 8/2011 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*

International Search Report issued by the International Searching Authority (ISA/O.E.P.M.) dated Jun. 10, 2014 in connection with International Application No. PCT/EP2014/055158.
Uniprot accession No. Q72JW2, Unreviewed; 293 AA, XP002699949, Jul. 5, 2004, "Subname: Full=Hypothetical conserved protein;", including Henne, A. et al., "The genome sequence of the extreme thermophile Thermus thermophiles", Nature Biotechnology, vol. 22, No. 5, 2004, pp. 547-553.
Lipps, G. et al., A novel type of replicative enzyme harbouring ATPase, primase and DNA polymerase activity, EMBO (European Molecular Biology Organization) Journal, vol. 22, No. 10, 2003, pp. 2516-2525.
Mcdonald, J.P. et al., "Novel thermostable Y-family polymerases: applications for the PCR amplification of damaged or ancient DNAs", Nucleic Acids Research, vol. 34, No. 4, 2006, pp. 1102-1111.
Alsmadi O., F. Alkayal et al., "Specific and complete human genome amplification with improved yield by phi29 DNA polymerase and a novel primer at elevated temperature." *BMC ResNotes* 2:48, (Mar. 24, 2009).
Altschul S. F. et al., "Basic local alignment search tool." JMolBiol 215(3): 403-410(1990).
Aravind L., et al., "Toprim—a conserved catalytic domain in type IA and II topoisomerases, DnaG-type primases, OLD family nucleases and RecR proteins." Nucleic Acids Res 26(18): 4205-4213, (1998).
Bentley D. R., S. Balasubramanian et al., "Accurate whole human genome sequencing using reversible terminator chemistry." Nature 456(7218): 53-59, (2008).
Bernad A., L. Blanco et al., "A conserved 3'-5' exonuclease active site in prokaryotic and eukaryotic DNA polymerases." Cell 59(1): 219-228, (1989).
Berquist B. R. and D. M. Wilson, 3rd "Pathways for repairing and tolerating the spectrum of oxidative DNA lesions." Cancer Lett 327(1-2): 61-72, (2012).
Blainey et al., "Digital Mda For Enumeration of Total Nucleic Acid Contamination" Nucleic Acids Research vol. 39, No. 4, (2011).
Branton D., D. W. Deamer, et al., "The Potential and Challenges of Nanopore Sequencing" Nat Biotechnol 26(10): 1146-1153, (2008).
Butler T. Z., M. Pavlenok, et al., "Single-Molecule DNA Detection With an Engineered MspA Protein Nanopore" Proc Natl Acad Sci U S A 105(52): 20647-20652, (2008).
Cavanaugh N. A. and R. D. Kuchta, "Initiation of new DNA strands by the herpes simplex virus-1 primase-helicase complex and either herpes DNA polymerase or human DNA polymerase alpha." J Biol Chem 284(3): 1523-1532, (2009).
Champlot S., et al., "An Efficient Multistrategy DNA Decontamination Procedure of PCR Reagents for Hypersensitive PCR Applications". PLoS One 5(9), (2010).
Chemnitz Galal W., et al., "Characterization of DNA primase complex isolated from the archaeon, Thermococcus kodakaraensis." J Biol Chem 287(20): 16209-16219, (2012).
Clarke J., et al., "Continuous Base Identification For Single-Molecule Nanopore DNA sequencing." Nat Nanotechnol 4(4): 265-270, (2009).

(Continued)

*Primary Examiner* — Richard G Hutson
(74) *Attorney, Agent, or Firm* — Gary J. Gershik

(57) ABSTRACT

The present invention is directed to methods for replicating, amplifying, and sequencing of nucleic acids using the thermostable, bifunctional replicase "TthPrimPol" from *Thermus thermophilus* HB27. The TthPrimPol enzyme is extremely tolerant to alterations of the nucleotides of the template nucleic acid. Therefore, in one aspect the invention discloses methods for replicating, amplifying and sequencing of damaged polynucleotide templates.

19 Claims, 20 Drawing Sheets

Specification includes a Sequence Listing.

(56) References Cited

OTHER PUBLICATIONS

Corless et al., "Contamination and Sensitivity Issues with a Real-TimeUniversal 16S rRNA PCR" Journal of Clinical Microbiology, p. 1747-1752, May 2000.
Derrington I. M., et al., "Nanopore DNA sequencing with MspA." Proc Natl Acad Sci U S A 107(37): 16060-16065, (2010).
Eid, J., et al., "Real-time DNA sequencing from single polymerase molecules." Science 323(5910): 133-8, (2009).
Ewing B, Hillier L, Wendl MC, Green P, "Base-calling of automated sequencer traces using phred. I. Accuracy assessment". Genome Res. 8 (3) : 175-185, (1998).
Frick D. N. and C. C. Richardson, "DNA primases." Annu Rev Biochem 70: 39-80, (2001).
García Gómez et al., "PrimPol a two in one enzyme: primase and bypass polymerase", From Single Molecules to System Biology. Sevilla, IUBMB FEBS, (2012).
Gerard et al., "Reverse Transcriptase. The Use of Cloned Moloney Murine Leukemia Virus Reverse Transcriptase to Synthesize DNA from RNA." Mol Biotechnol 8(1): 61-77, (1997).
Guo J. et al., "Four-color DNA sequencing with 3â€²-O-modified nucleotide reversible terminators and chemically cleavable fluorescent dideoxynucleotides." Proceedings of the National Academy of Sciences 105(27):9145-9150, (2008).
Han T. et al., "Characterization of whole genome amplified (WGA) DNA for use in genotyping assay development" BMC Genomics, 13:217, (2012).
Hein et al., "Ethidium monazide and propidium monoazide for elimination of unspecific DNA background in quantitative universal real-time PCR" Journal of Microbiological Methods 71,336-339, (2007).
Hinz H. J. et al., "Fundamentals of protein stability." Pure & Appl. Chem. 65(5): 5, (1993).
Holmes A. M. et al., "Initiation of DNA synthesis by the calf thymus DNA polymerase-primase complex." J Biol Chem 260(19): 10840-6, (1985).
Hosono et al., "Unbiased Whole-Genome Amplification Directly from Clinical Samples" Genome Res 13:954-964) (2003).
Ilyina T. V. and E. V. Koonin, "Conserved sequence motifs in the initiator proteins for rolling circle DNA replication encoded by diverse replicons from eubacteria, eucaryotes and archaebacteria." Nucleic Acids Res 20(13): 3279-85, (1992).
Iyer L. M. et al., "Origin and evolution of the archaeo-eukaryotic primase superfamily and related palm-domain proteins: structural insights and new members." Nucleic Acids Res 33(12): 3875-96, (2005).
Jetha N. N. et al., "Forming an alpha-hemolysin nanopore for single-molecule analysis." Methods Mol Biol 544: 113-27, (2009).
Ju J. et al., "Four-color DNA sequencing by synthesis using cleavable fluorescent nucleotide reversible terminators." Proceedings of the National Academy of Sciences 103(52): 19635-19640, (2006).
Kim Y. H. et al., "Comparing the effect on protein stability of methionine oxidation versus mutagenesis: steps toward engineering oxidative resistance in proteins." Protein Eng 14(5): 343-7, (2001).
Lage et al., "Whole Genome Analysis of Genetic Alterations in Small DNA Samples using Hyperbranched Strands Displaced Amplification and Array-CGH" Genome Res 13:294-307, (2003).
Lao-Sirieix S. H. and S. D. Bell "The heterodimeric primase of the hyperthermophilic archaeon Sulfolobus solfataricus possesses DNA and RNA primase, polymerase and 3'-terminal nucleotidyl transferase activities." J Mol Biol 344(5): 1251-63, (2004).
Lao-Sirieix S. H. et al., "The promiscuous primase." Trends Genet 21(10): 568-72, (2005).
Lieberman K. R. et al., "Processive replication of single DNA molecules in a nanopore catalyzed by phi29 DNA polymerase." J Am Chem Soc 132(50): 17961-72, (2010).
Lipps, G. "The replication protein of the Sulfolobus islandicus plasmid pRN1." Biochem Soc Trans 32(Pt 2): 240-4, (2004).
Lipps G., et al., "A novel type of replicative enzyme harbouring ATPase, primase and DNA polymerase activity." EMBO J 22(10): 2516-25, (2003).
Lipps, G. et al., "Structure of a bifunctional DNA primase-polymerase." Nat Struct Mol Biol 11(2): 157-62, (2004).
Litosh, V. A. et al., "Improved nucleotide selectivity and termination of 3'-OH unblocked reversible terminators by molecular tuning of 2-nitrobenzyl alkylated HOMedU triphosphates." Nucleic Acids Res 39(6): e39, (2011).
Macaulay IC, Voet T "Single Cell Genomics: Advances and Future Perspectives". PLoS Genet 10(1), (2014).
Maglia G. et al., "Enhanced translocation of single DNA molecules through alpha-hemolysin nanopores by manipulation of internal charge." Proc Natl Acad Sci U S A 105(50): 19720-5, (2008).
Manrao E. A. et al., "Reading DNA at single-nucleotide resolution with a mutant MspA nanopore and phi29 DNA polymerase." Nat Biotechnol 30(4): 349-53, (2012).
Manrao E. A. et al., "Nucleotide discrimination with DNA immobilized in the MspA nanopore." PLoS One 6(10): e25723, (2011).
Maxam A. M. and W. Gilbert "A new method for sequencing DNA." Proc Natl Acad Sci U S A 74(2): 560-4, (1977).
Metzker M. L. "Sequencing technologies—the next generation." Nat Rev Genet 11(1): 31-46, (2009).
Moser M. J. et al., "Thermostable DNA polymerase from a viral metagenome is a potent RT-PCR enzyme." PLoS One 7(6): e38371, (2012).
Myers T. W. and D. H. Gelfand "Reverse transcription and DNA amplification by a Thermus thermophilus DNA polymerase." Biochemistry 30(31): 7661-6, (1991).
Newrzella D. et al., "The functional genome of CA1 and CA3 neurons under native conditions and in response to ischemia." BMC Genomics 8: 370, (2007).
Paez et al., "Genome coverage and sequence lodelity of Φ29 polymerese-based multiple strand displacement whole genome amplification" Nucleic Acids Res 32:e71, (2004).
Parker, W. B. and Y. C. Cheng "Inhibition of DNA primase by nucleoside triphosphates and their arabinofuranosyl analogs." Mol Pharmacol 31(2): 146-51, (1987).
Pavlenok, M., I. M. Derrington, et al., "MspA nanopores from subunit dimers." PLoS One 7(6): e38726, (2012).
Pinard et al., "Assesment of whole genome amplification-induced bias through high-throughput, massively parallel whole genome sequenceing", BMC Genomics 7:216. (2006).
Pugh et al., "Impact of whole genome amplification on analysis of copy number variants", Nucleic Acids Research vol. 36, No. 13(2008).
Raghunathan et al., "Genomic DNA Amplification from a Single Bacterium" Appl Environ Microbiol 71:3342-3347(2005).
Ronaghi M., S. Karamohamed, et al., "Real-time DNA sequencing using detection of pyrophosphate release." Anal Biochem 242(1): 84-9(1996).
Ronaghi M. et al., "A sequencing method based on real-time pyrophosphate." Science 281(5375): 363, 365(1998).
Rossner M. J. et al., "Global transcriptome analysis of genetically identified neurons in the adult cortex." J Neurosci 26(39): 9956-66(2006).
Salas, M. "Protein-priming of DNA replication." Annu Rev Biochem 60: 39-71 (1991).
Sam L. T. et al., "A comparison of single molecule and amplification based sequencing of cancer transcriptomes." PLoS One 6(3): e17305 (2011).
Sanchez-Berrondo J. et al.,"Molecular architecture of a multifunctional MCM complex." Nucleic Acids Res 40(3): 1366-80(2011).
Sanger F. and A. R. Coulson, "The use of thin acrylamide gels for DNA sequencing." FEBS Lett 87(1): 107-110 (1978).
Sanger F. et al., "DNA sequencing with chain-terminating inhibitors." Proc Natl Acad Sci U S A 74(12): 5463-7 (1977).
Schoenfeld T. et al., "Functional viral metagenomics and the next generation of molecular tools." Trends Microbiol 18(1): 20-9 (2009).
Schoenfeld T. et al., "Assembly of viral metagenomes from yellowstone hot springs." Appl Environ Microbiol 74(13): 4164-74 (2008).
Silander K. and J. Saarela, "Whole genome amplification with Phi29 DNA polymerase to enable genetic or genomic analysis of samples of low DNA yield." Methods Mol Biol 439: 1-18 (2008).

(56) References Cited

OTHER PUBLICATIONS

Simpson R. J., "Stabilization of proteins for storage." Cold Spring Harb Protoc 2010(5): pdb top79 (2005).
Spits C., et al., "Optimization and evaluation of single-cell whole-genome multiple displacement amplification." Hum Mutat 27(5): 496-503 (2006).
Spits C., et al., "Whole-genome multiple displacement amplification from single cells." Nat Protoc 1(4): 1965-70 (2006).
Thompson J. F. and P. M. Milos, "The properties and applications of single-molecule DNA sequencing." Genome Biol 12(2): 217 (2011).
Turcatti G., et al., "A new class of cleavable fluorescent nucleotides: synthesis and optimization as reversible terminators for DNA sequencing by synthesis." Nucleic Acids Research 36(4): e25 (2008).
Wendell D., et al., "Translocation of double-stranded DNA through membrane-adapted phi29 motor protein nanopores." Nat Nanotechnol 4(11): 765-72 (2009).
Woyke T, et al., "Decontamination of MDA Reagents for Single Cell Whole Genome Amplification". PLoS One 6(10) (2011).
Wu, W., et al., "Termination of DNA synthesis by N6-alkylated, not 3'-O-alkylated, photocleavable 2'-deoxyadenosine triphosphates." Nucleic Acids Res 35(19): 6339-49 (2007).
Zhang L. et al., "Whole genome amplification from a single cell: implications for genetic analysis". Proc Natl Acad Sci U S A 89: 5847-5851, (1992).
Accession No. AAS81004, "Hypothetical conserved protein [Thermus thermophilus HB27]", Mar. 2010.
Accession No. AEG33442, "Bifunctional DNA primase/polymerase [Thermus thermophlus SG0.5JP17-16]", Oct. 2011.
FEBS Journal 279 (Supplement 1), p. 485, 2012.
Katafuchi, A. and Nohmi, T., "DNA polymerases involved in the incorporation of oxidized nucleotides into DNA: Their efficiency and template base preference". Mutation Research, 2010, vol. 703, pp. 24-31.
Sikorsky, J.A. et al., "DNA damage reduces Taq DNA polymerase fidelity and PCR amplification efficiency". Biochemical and Biophysical Research Communications, 2007, vol. 355, pp. 431-437.

* cited by examiner

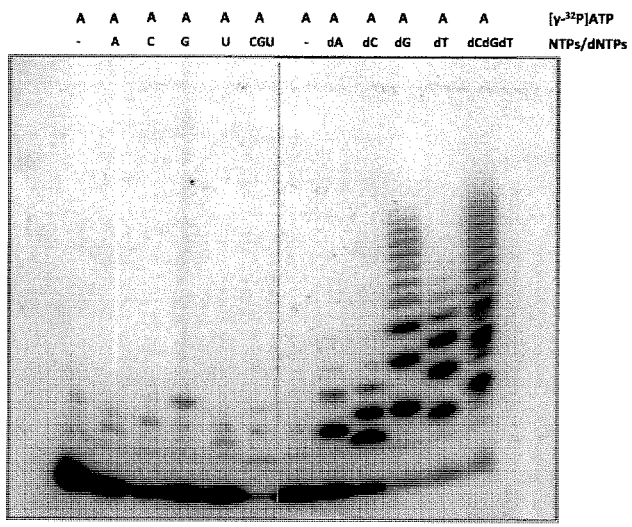
Figure 3:
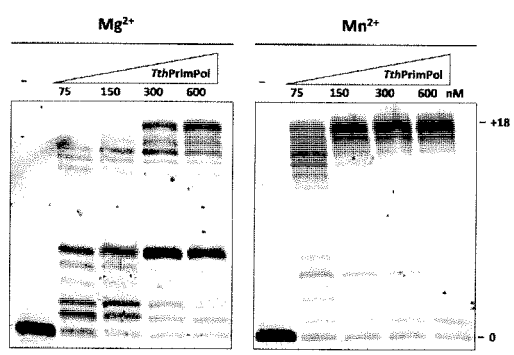
Figure 4

```
>SEQ ID NO: 1
MRPIEHALSYAAQGYGVLPLRPGGKEPLGKLVPHGLKNASRDPATLEAWWRSCPRCGVGILP
GPEVLVLDFDDPEAWEGLRQEHPALEAAPRQRTPKGGRHVFLRLPEGVRLSASVRAIPGVDL
RGMGRAYVVAAPTRLKDGRTYTWEAPLTPPEELPPVPQALLLKLLPPPPPPRPSWGAVGTAS
PKRLQALLQAYAAQVARTPEGQRHLTLIRYAVAAGGLIPHGLDPREAEEVLVAAAMSAGLPE
WEARDAVRWGLGVGASRPLVLESSSKPPEPRTYRARVYARMRRWV

>SEQ ID NO: 2
MGSSHHHHHHSSGLVPRGSHMRPIEHALSYAAQGYGVLPLRPGGKEPLGKLVPHGLKNASRDP
ATLEAWWRSCPRCGVGILPGPEVLVLDFDDPEAWEGLRQEHPALEAAPRQRTPKGGRHVFLRL
PEGVRLSASVRAIPGVDLRGMGRAYVVAAPTRLKDGRTYTWEAPLTPPEELPPVPQALLLKLL
PPPPPPRPSWGAVGTASPKRLQALLQAYAAQVARTPEGQRHLTLIRYAVAAGGLIPHGLDPRE
AEEVLVAAAMSAGLPEWEARDAVRWGLGVGASRPLVLESSSKPPEPRTYRARVYARMRRWV

>SEQ ID NO: 3
TTTTTTTTTTTTTTTCCTGTTTTTTTTTT

>SEQ ID NO: 4
TTTTTTTTTTTTTTTCCTXTTTTTTTTTT

>SEQ ID NO: 5
GTACCCGGGGATCCGTACGGCGCATCAGCTGCAG

>SEQ ID NO: 6
CTGCAGCTGATGCGCC

>SEQ ID NO: 7
ACTGGCCGTCGTTCTATTGTACTCACTGTGATC

>SEQ ID NO: 8
GATCACAGTGAGTAC

>SEQ ID NO: 9
AACGACGGCCAGT

>SEQ ID NO: 10
AGAAGTGTATCTTGTACTCACTGTGATC

>SEQ ID NO: 11
CCGGCCCATATGAGGCCGATTGAGCACGCCC

>SEQ ID NO: 12
AGAAGUGUAUCUUGUACUCACUGUGAUC

>SEQ ID NO: 13
CTGCAGCTGATGCGCXGTACGGATCCCCGGGTAC

>SEQ ID NO: 14
GTACCCGGGGATCCGTAC

>SEQ ID NO: 15
TTTTTTTTTTTTTT

>SEQ ID NO: 16
AAAAAAAAAAAAAA

>SEQ ID NO: 17
GCGCGCGAATTCTCATACCCACCTCCTCATCCGGG
```

Figure 24

| | Sample | Count | Percentage of reads | Average length | Number of bases | Percentage of bases |
|---|---|---|---|---|---|---|
| Mapped reads | | 2.573.771 | 91,92% | 253,21 | 651.711.875 | 93,41% |
| Not mapped reads | Tth-100/Phi | 226.201 | 8,08% | 203,14 | 45.949.636 | 6,59% |
| Total reads | | 2.799.972 | 100,00% | 249,17 | 697.661.511 | 100,00% |
| Mapped reads | | 2.533.407 | 90,48% | 254,79 | 645.478.540 | 91,25% |
| Not mapped reads | Tth-200/Phi | 266.565 | 9,52% | 232,16 | 61.885.052 | 8,75% |
| Total reads | | 2.799.972 | 100,00% | 252,63 | 707.363.592 | 100,00% |
| Mapped reads | | 2.349.664 | 83,92% | 254,87 | 598.866.336 | 89,94% |
| Not mapped reads | RP | 450.258 | 16,08% | 148,84 | 67.017.422 | 10,06% |
| Total reads | | 2.799.922 | 100,00% | 237,82 | 665.883.758 | 100,00% |
| Mapped reads | | 2.570.299 | 91,80% | 260,15 | 668.666.985 | 95,36% |
| Not mapped reads | NA | 229.643 | 8,20% | 141,75 | 32.551.077 | 4,64% |
| Total reads | | 2.799.942 | 100,00% | 250,44 | 701.218.062 | 100,00% |

| Reference | Tth-100/Phi | | | RP | | | NA | | |
|---|---|---|---|---|---|---|---|---|---|
| | Reads | Length | Signatures | Reads | Length | Signatures | Reads | Length | Signatures |
| chr01_BY4741 | 49.200 | 230.221 | 141 | 43.615 | 230.221 | 173 | 49.902 | 230.221 | 96 |
| chr02_BY4741 | 163.037 | 813.172 | 421 | 154.626 | 813.172 | 536 | 154.393 | 813.172 | 199 |
| chr03_BY4741 | 60.754 | 316.620 | 225 | 64.010 | 316.620 | 242 | 64.803 | 316.620 | 142 |
| chr04_BY4741 | 303.201 | 1.531.933 | 839 | 288.631 | 1.531.933 | 1.061 | 277.857 | 1.531.933 | 393 |
| chr05_BY4741 | 125.522 | 576.874 | 341 | 115.451 | 576.874 | 441 | 117.228 | 576.874 | 195 |
| chr06_BY4741 | 62.177 | 270.161 | 186 | 60.104 | 270.161 | 190 | 57.101 | 270.161 | 92 |
| chr07_BY4741 | 221.523 | 1.090.941 | 521 | 202.750 | 1.090.941 | 772 | 202.398 | 1.090.941 | 293 |
| chr08_BY4741 | 121.616 | 562.641 | 347 | 108.334 | 562.641 | 351 | 115.570 | 562.641 | 156 |
| chr09_BY4741 | 99.845 | 439.890 | 257 | 87.148 | 439.890 | 274 | 90.709 | 439.890 | 139 |
| chr10_BY4741 | 152.952 | 745.751 | 420 | 136.183 | 745.751 | 523 | 146.790 | 745.751 | 219 |
| chr11_BY4741 | 144.347 | 666.813 | 386 | 129.798 | 666.813 | 482 | 128.956 | 666.813 | 189 |
| chr12_BY4741 | 284.192 | 1.078.180 | 884 | 248.328 | 1.078.180 | 959 | 437.999 | 1.078.180 | 787 |
| chr13_BY4741 | 197.248 | 924.428 | 487 | 173.647 | 924.428 | 556 | 176.070 | 924.428 | 265 |
| chr14_BY4741 | 176.831 | 784.331 | 450 | 152.806 | 784.331 | 522 | 152.875 | 784.331 | 198 |
| chr15_BY4741 | 218.242 | 1.091.288 | 595 | 199.820 | 1.091.288 | 668 | 204.714 | 1.091.288 | 273 |
| chr16_BY4741 | 192.097 | 948.066 | 499 | 182.585 | 948.066 | 695 | 178.277 | 948.066 | 243 |
| chr17_BY4741 | 987 | 85.779 | 21 | 1.828 | 85.779 | 24 | 14.657 | 85.779 | 80 |
| Total | 2.573.771 | 12.157.089 | 7.020 | 2.349.664 | 12.157.089 | 8.469 | 2.570.299 | 12.157.089 | 3.959 |

Figure 29

SEQUENCE LISTING

<160> NUMBER OF SEQ ID NOS: 17

<210> SEQ ID NO 1
<211> LENGTH: 293
<212> TYPE: PRT
<213> ORGANISM: Thermus thermophilus

<400> SEQUENCE: 1

Met Arg Pro Ile Glu His Ala Leu Ser Tyr Ala Ala Gln Gly Tyr Gly
1               5                   10                  15

Val Leu Pro Leu Arg Pro Gly Gly Lys Glu Pro Leu Gly Lys Leu Val
            20                  25                  30

Pro His Gly Leu Lys Asn Ala Ser Arg Asp Pro Ala Thr Leu Glu Ala
                35                  40                  45

Trp Trp Arg Ser Cys Pro Arg Cys Gly Val Gly Ile Leu Pro Gly Pro
 50                  55                  60

Glu Val Leu Val Leu Asp Phe Asp Pro Glu Ala Trp Gly Leu
 65                  70                  75                  80

Arg Gln Glu His Pro Ala Leu Glu Ala Ala Pro Arg Gln Arg Thr Pro
                 85                  90                  95

Lys Gly Gly Arg His Val Phe Leu Arg Leu Pro Glu Gly Val Arg Leu
                100                 105                 110

Ser Ala Ser Val Arg Ala Ile Pro Gly Val Asp Leu Arg Gly Met Gly
            115                 120                 125

Arg Ala Tyr Val Val Ala Ala Pro Thr Arg Leu Lys Asp Gly Arg Thr
        130                 135                 140

Tyr Thr Trp Glu Ala Pro Leu Thr Pro Pro Glu Glu Leu Pro Pro Val
145                 150                 155                 160

Pro Gln Ala Leu Leu Leu Lys Leu Leu Pro Pro Pro Pro Pro Pro Arg
                165                 170                 175

Pro Ser Trp Gly Ala Val Gly Thr Ala Ser Pro Lys Arg Leu Gln Ala
                180                 185                 190

Leu Leu Gln Ala Tyr Ala Ala Gln Val Ala Arg Thr Pro Glu Gly Gln
            195                 200                 205

Arg His Leu Thr Leu Ile Arg Tyr Ala Val Ala Ala Gly Gly Leu Ile
        210                 215                 220

Pro His Gly Leu Asp Pro Arg Glu Ala Glu Glu Val Leu Val Ala Ala
225                 230                 235                 240

Ala Met Ser Ala Gly Leu Pro Glu Trp Glu Ala Arg Asp Ala Val Arg
                245                 250                 255

Trp Gly Leu Gly Val Gly Ala Ser Arg Pro Leu Val Leu Glu Ser Ser
                260                 265                 270

Ser Lys Pro Pro Glu Pro Arg Thr Tyr Arg Ala Arg Val Tyr Ala Arg
            275                 280                 285

Met Arg Arg Trp Val
            290

<210> SEQ ID NO 2
<211> LENGTH: 313
<212> TYPE: PRT
<213> ORGANISM: Thermus thermophilus
<220> FEATURE:
<223> OTHER INFORMATION: PrimPol + His Tag

<400> SEQUENCE: 2

Met Gly Ser Ser His His His His His His Ser Ser Gly Leu Val Pro
1               5                   10                  15

Arg Gly Ser His Met Arg Pro Ile Glu His Ala Leu Ser Tyr Ala Ala
            20                  25                  30

Gln Gly Tyr Gly Val Leu Pro Leu Arg Pro Gly Gly Lys Glu Pro Leu
        35                  40                  45

Gly Lys Leu Val Pro His Gly Leu Lys Asn Ala Ser Arg Asp Pro Ala
    50                  55                  60

Thr Leu Glu Ala Trp Trp Arg Ser Cys Pro Arg Cys Gly Val Gly Ile
65                  70                  75                  80

Leu Pro Gly Pro Glu Val Leu Val Leu Asp Phe Asp Asp Pro Glu Ala
                85                  90                  95

-continued

```
Trp Glu Gly Leu Arg Gln Glu His Pro Ala Leu Glu Ala Ala Pro Arg
            100                 105                 110

Gln Arg Thr Pro Lys Gly Gly Arg His Val Phe Leu Arg Leu Pro Glu
        115                 120                 125

Gly Val Arg Leu Ser Ala Ser Val Arg Ala Ile Pro Gly Val Asp Leu
    130                 135                 140

Arg Gly Met Gly Arg Ala Tyr Val Val Ala Ala Pro Thr Arg Leu Lys
145                 150                 155                 160

Asp Gly Arg Thr Tyr Thr Trp Glu Ala Pro Leu Thr Pro Pro Glu Glu
                165                 170                 175

Leu Pro Pro Val Pro Gln Ala Leu Leu Leu Lys Leu Leu Pro Pro Pro
            180                 185                 190

Pro Pro Pro Arg Pro Ser Trp Gly Ala Val Gly Thr Ala Ser Pro Lys
        195                 200                 205

Arg Leu Gln Ala Leu Leu Gln Ala Tyr Ala Ala Gln Val Ala Arg Thr
    210                 215                 220

Pro Glu Gly Gln Arg His Leu Thr Leu Ile Arg Tyr Ala Val Ala Ala
225                 230                 235                 240

Gly Gly Leu Ile Pro His Gly Leu Asp Pro Arg Glu Ala Glu Glu Val
                245                 250                 255

Leu Val Ala Ala Ala Met Ser Ala Gly Leu Pro Glu Trp Glu Ala Arg
            260                 265                 270

Asp Ala Val Arg Trp Gly Leu Gly Val Gly Ala Ser Arg Pro Leu Val
        275                 280                 285

Leu Glu Ser Ser Ser Lys Pro Pro Glu Pro Arg Thr Tyr Arg Ala Arg
    290                 295                 300

Val Tyr Ala Arg Met Arg Arg Trp Val
305                 310

<210> SEQ ID NO 3
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="template DNA"
      /organism="Artificial Sequence"

<400> SEQUENCE: 3
tttttttttt tttttcctgt tttttttt                                  29

<210> SEQ ID NO 4
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="template DNA"
      /organism="Artificial Sequence"

<400> SEQUENCE: 4
tttttttttt tttttcctnt tttttttt                                  29

<210> SEQ ID NO 5
<211> LENGTH: 34
<212> TYPE: DNA
```

```
<213> ORGANISM: Artificial Sequence
<220> FEATURE:
<221> NAME/KEY: source
<222> LOCATION: 1..34
<223> OTHER INFORMATION: /mol_type="unassigned DNA"
      /note="template DNA"
      /organism="Artificial Sequence"

<400> SEQUENCE: 5
gtacccgggg atccgtacgg cgcatcagct gcag                              34

<210> SEQ ID NO 6
<211> LENGTH: 16
<212> TYPE: DNA
<213> ORGANISM: Artificial Sequence
<220> FEATURE:
<221> NAME/KEY: source
<222> LOCATION: 1..16
<223> OTHER INFORMATION: /mol_type="unassigned DNA"
      /note="primer"
      /organism="Artificial Sequence"

<400> SEQUENCE: 6
ctgcagctga tgcgcc                                                  16

<210> SEQ ID NO 7
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="unassigned DNA"
      /note="template DNA"
      /organism="Artificial Sequence"

<400> SEQUENCE: 7
actggccgtc gttctattgt actcactgtg atc                               33

<210> SEQ ID NO 8
<211> LENGTH: 15
<212> TYPE: DNA
<213> ORGANISM: Artificial Sequence
<220> FEATURE:
<221> NAME/KEY: source
<222> LOCATION: 1..15
<223> OTHER INFORMATION: /mol_type="unassigned DNA"
      /note="primer"
      /organism="Artificial Sequence"

<400> SEQUENCE: 8
gatcacagtg agtac                                                   15

<210> SEQ ID NO 9
<211> LENGTH: 13
<212> TYPE: DNA
<213> ORGANISM: Artificial Sequence
<220> FEATURE:
<221> NAME/KEY: source
<222> LOCATION: 1..13
<223> OTHER INFORMATION: /mol_type="unassigned DNA"
      /note="primer"
      /organism="Artificial Sequence"

<400> SEQUENCE: 9
aacgacggcc agt                                                     13

<210> SEQ ID NO 10
<211> LENGTH: 28
```

```
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="template DNA"
      /organism="Artificial Sequence"

<400> SEQUENCE: 10
agaagtgtat cttgtactca ctgtgatc                                          28

<210> SEQ ID NO 11
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="unassigned DNA"
      /note="primer"
      /organism="Artificial Sequence"

<400> SEQUENCE: 11
ccggcccata tgaggccgat tgagcacgcc c                                      31

<210> SEQ ID NO 12
<211> LENGTH: 28
<212> TYPE: RNA
<213> ORGANISM: Artificial Sequence
<220> FEATURE:
<221> NAME/KEY: source
<222> LOCATION: 1..28
<223> OTHER INFORMATION: /mol_type="unassigned RNA"
      /note="template RNA"
      /organism="Artificial Sequence"

<400> SEQUENCE: 12
agaaguguau cuuguacuca cugugauc                                          28

<210> SEQ ID NO 13
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="unassigned DNA"
      /note="template DNA"
      /organism="Artificial Sequence"

<400> SEQUENCE: 13
ctgcagctga tgcgcngtac ggatccccgg gtac                                   34

<210> SEQ ID NO 14
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="unassigned DNA"
      /note="primer"
      /organism="Artificial Sequence"

<400> SEQUENCE: 14
gtacccgggg atccgtac                                                     18

<210> SEQ ID NO 15
```

```
<211> LENGTH: 14
<212> TYPE: DNA
<213> ORGANISM: Artificial Sequence
<220> FEATURE:
<221> NAME/KEY: source
<222> LOCATION: 1..14
<223> OTHER INFORMATION: /mol_type="unassigned DNA"
      /note="poly-t"
      /organism="Artificial Sequence"

<400> SEQUENCE: 15
tttttttttt tttt                                                      14

<210> SEQ ID NO 16
<211> LENGTH: 14
<212> TYPE: DNA
<213> ORGANISM: Artificial Sequence
<220> FEATURE:
<221> NAME/KEY: source
<222> LOCATION: 1..14
<223> OTHER INFORMATION: /mol_type="unassigned DNA"
      /note="poly-a"
      /organism="Artificial Sequence"

<400> SEQUENCE: 16
aaaaaaaaaa aaaa                                                      14

<210> SEQ ID NO 17
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="unassigned DNA"
      /note="primer"
      /organism="Artificial Sequence"

<400> SEQUENCE: 17
gcgcgcgaat tctcataccc acctcctcat ccggg                               35
```

METHODS FOR AMPLIFICATION AND SEQUENCING USING THERMOSTABLE TTHPRIMPOL

In a broad sense, the present invention is directed to a thermostable primase/polymerase protein TthPrimPol of the thermophile bacterial strain *Thermus thermophilus* HB27 and its use in methods for synthesizing, amplifying and sequencing nucleic acids. Amongst others, the present invention discloses primer-free methods, comprising TthPrimPol, for amplification of damaged DNA or RNA, as well as tool and kits comprising said protein.

BACKGROUND OF THE INVENTION

In almost all DNA replication systems known so far, the initiation of replication requires a free hydroxyl group to be the acceptor of the nucleotides added by DNA polymerases. For this task, several different solutions have been described: in all cellular life forms, as well as many viruses and plasmids, a specialized RNA polymerase called "primase" polymerizes ribonucleotides, generating a short RNA primer that is subsequently elongated by a DNA polymerase (Kornberg and Baker 1991). In retroelements and retrovruses, reverse transcriptases use a tRNA to initiate replication (Lodish, Berk et al. 1999). In protein-primed systems from viruses like the bacteriophage Phi29, the OH group from the side-chain of a specific serine, threonine or tyrosine is used as the initial site for DNA replication (Salas 1991). Finally, in viruses that follow the rolling circle replication model, an endonuclease creates a nick in one of the DNA strands, generating a free 3'OH group that is elongated by a DNA polymerase (Ilyina and Koonin 1992; Noirot-Gros and Ehrlich 1996).

Primases can be divided in two evolutionarily unrelated families: DnaG-like primases (Bacteria) and AEP-like primases (Archasa and Eukaryotes) (Aravind, Leipe et al. 1998; Iyer, Koonin et al. 2005). Recently a novel subfamily of AEPs called "PrimPol" (Lipps 2004; Lipps, Weinzied et al. 2004) has been described, which is also sporadically present in Gram-positive bacterial plasmids. PrimPols show both DNA polymerase and RNA primase activities, and are often associated to helicases in order to form a replication initiation complex. These features enable a system where the same enzyme performs both the initiation and elongation stages. And just recently a helicase which also comprises primase and polymerase activity has been described (Sanchez-Berrondo. Mesa et al. 2011). Unlike eukaryotic primases, archeal primases are able to carry out the initiation and extension of both RNA and DNA chains of up to 1 kb or 7 kb, respectively (Chemitz Galal, Pan et al. 2012; Lao-Sirieix and Bell 2004; Lao-Sirieix, Pellegrini et al. 2005). Further enzymatic properties of specific PrimPol family members have recently been described, for example García Gómez demonstrated that the human PrimPol (HsPrimPol), encoded by the human PRIMPOL gene (also known as CCDC111), is able to bypass abasic sites like oxidative nucleotide modifications of template DNA and a role in DNA maintenance and re-initiation of arrested replication forks has been proposed. (García Gómez. Martinez Jiménez et al. 2012), whereas the thermostable primpol of *Thermococcus nautilus* 30/1 plasmid pTN2 comprises terminal transferase activity (WO 2011/098588).

The hypothetical conserved protein AAS81004.1 from *Thermus thermophilus* HB27, predicted to contain a primase-polymerase (PrimPol) domain of the type found in bifunctional replicases from archaeal plasmids, including ORF904 protein of the crenarchaeal plasmid pRN1 from *Sufolobus islandicus* (pRN1 primpol), was cloned, overexpressed in *E. coli* in a soluble and active form, and purified to homogeneity. While deeply characterizing the enzymatic properties of the isolated protein (hereinbelow named as TthPrimPol), the inventors surprisingly found that beside the predicted primase activity, the protein reveals an unexpected high tolerance to damaged or tainted templates, allowing for the development of new amplification and sequencing methods.

Amplification of nucleic acids, for example by polymerase chain reaction (PCR) as introduced by Mullis (U.S. Pat. No. 5,656,493) is an indispensable technique used in medical and biological research. It has been successfully applied to a variety of applications like cloning, manipulating or sequencing of nucleic acids, DNA-based functional and phylogenetic analysis of genes, detection and diagnosis of diseases, as well as in forensic science and paternity testing.

As of today, a number of different sequencing techniques exist, that are commonly subsummized under first generation sequencing, second generation sequencing, or often called next generation sequencing (NGS), and third generation, or single molecule sequencing (SMS). First generation sequencing refers mainly to the methods of Maxam and Gilbert (Maxam and Gilbert 1977) or Sanger (Sanger, Nicklen et al. 1977; Sanger and Coulson 1978), of which only the latter is used today.

Second, or next generation sequencing refers to techniques that produce many sequences at the same time using advanced technical (optical) detection methods of base positions. An overview over existing methods is given in (Metzker 2009).

Third generation or single molecule sequencing (SMS) techniques do not require prior amplification, and sequence not clones or ensembles of DNA, but single molecules, often in "real time", meaning the online recording of the activity of a polymerase (Sam, Lipson et al. 2011; Thompson and Milos 2011).

Nevertheless, there still is a great need for a new thermostable, highly processive polymerase belonging to the primpol DNA/RNA polymerase family which can work at high temperature and which is able to produce long extension products, preferably more than 5 Kb in length, without the need of the presence of additional proteins.

Particularly awaited is a thermostable DNA polymerase which is easy to produce and exhibits a DNA primase activity and is consequently able to synthesize or amplify unknown DNA templates, preferably in absence of primers and which is able to produce with fidelity long extension products.

Especially in the field of forensic and clinical amplification applications as well as in second and third generation sequencing, a polymerase that is highly tolerant to a variety of substrate nucleotides, as well as being able to handle modified templates of often poor quality is of particular interest.

Accordingly, it is one of the objects of the present invention to provide methods for the amplification, especially for the primer-free amplification of DNA or RNA templates, even if said templates are of poor quality.

In a further object the present invention provides methods for reverse transcription of RNA with fidelity, even at high temperature.

These and other objects are considered to be solved by the subject-matter of the present invention disclosed herein below and in the claims.

SUMMARY OF THE INVENTION

The invention relates to the subject-matter as defined herein and in the claims. Said subject-matter includes a method for replication, amplification or sequencing of nucleic acids comprising the steps: providing a TthPrimPol enzyme, and providing a template nucleic acid, and providing nucleotides and/or nucleotide analogues for incorporation in a complementary strand of nucleic acid, and providing a suitable buffer, and optionally providing one or more primers, and contacting the above mentioned materials for a suitable period of time, optionally at high temperature.

In other aspects, the present invention relates to a method for primer free amplification of DNA—optionally comprising cooperative synthesis of DNA by both of the two polymerases provided for the amplification reaction—comprising the steps: providing a TthPrimPol enzyme, and providing a second polymerase, in particular of Phi29-type, and providing a template nucleic acid, and providing nucleotides and/or nucleotide analogues for incorporation in a complementary strand of nucleic acid, and providing a suitable buffer, and contacting the above mentioned materials for a suitable period of time, optionally at high temperature.

In further aspects, the present invention relates to methods for cDNA synthesis or RT PCR comprising the steps: providing a TthPrimPol enzyme, and providing a template RNA, and providing dNTPs, and providing a suitable buffer, and optionally providing one or more primers, and contacting the above mentioned materials for a suitable period of time, optionally at high temperature.

SHORT DESCRIPTION OF THE FIGURES

FIG. 1 illustrates TthPrimPol DNA primase activity on a single-stranded oligonucleotide in which a potential primase recognition sequence (GTCC) is flanked by thymine residues (Cavanaugh and Kuchta 2009) according to the preferred template context for initiation of the priming reaction by several viral, prokaryotic and eukaryotic RNA primases (Holmes, Cheristhundam et al. 1985; Parker and Cheng 1987; Frick and Richardson 2001). Priming occurred only in front of the "TC" sequence, and there was no priming opposite the poly dT tracks. The nucleotide acting as the primer (5' position) can be either a ribonucleotide (ATP) or a deoxynucleotide (dATP) in the presence of manganese, but only a deoxynucleotide (dATP) when magnesium was the metal cofactor. Added nucleotides (3' position) must be deoxynucleotides (dGTP), regardless of the metal cofactor. Conditions: 1 µM DNA (SEQ ID NO: 3), 400 nM TthPrimPol, 5 mM $MgCl_2$, 1 mM $MnCl_2$, 16 nM [$\gamma$-$^{32}$P]ATP, 16 nM [$\alpha$-$^{32}$P]dATP, 10 µM GTP/dGTP, 60', 55° C.

FIG. 2 depicts that CTC is TthPrimPol's preferred template initiation site in thymidine-rich ssDNA context according to SEQ ID No: 4. There is a strong effect of the nucleotide preceding the template TC start site, with maximal primate activity when C is the nucleotide preceding the start site. Conditions: 1 µM DNA (SEQ ID NO: 4), 400 nM TthPrimPol+His tag, 5 mM $MgCl_2$, 1 mM $MnCl_2$, 16 nM [$\gamma$-$^{32}$P]ATP, 1 µM dGTP, 60 min at a temperature of 55° C.

FIG. 3 shows TthPrimPol's DNA primase activity on a single-stranded circular DNA template (M13mp18 ssDNA). TthPrimPol strictly depends on deoxynucleotides for synthesis, whereas virtually no products are generated in the presence of ribonucleotides. Conditions: 400 ng M13mp18 ssDNA, 400 nM TthPrimPol+His tag. 1 mM $MnCl_2$, 16 nM [$\gamma$-$^{32}$P]ATP, 100 nM ATP/dATP, 1 µM CTP/dCTP, 1 µM GTP/dGTP. 1 µM UTP/dTTP, 60 min at a temperature of 55° C.

FIG. 4 depicts TthPrimPol's DNA polymerization activity. The enzyme is able to completely extend a primer molecule (SEQ ID NO: 6) according to the offered template (SEQ ID NO: 5) by polymerizing deoxynucleotides. Magnesium and manganese are valid as metal cofactors for DNA polymerization, although manganese seems to be more efficient. Conditions: 5 nM DNA, 1 mM $MnCl_2$, 5 mM $MgCl_2$, 100 µM dNTPs, 60 min at a temperature of 40° C.

FIG. 5 illustrates TthPrimPol's DNA/RNA polymerization activity on gapped DNA double strands, formed of SEQ ID NOs 7-9. Lower efficiency is observed in the case of RNA polymerization and seems to be strictly dependent on manganese. Moreover, manganese strongly stimulates strand-displacement synthesis on gapped DNA, allowing the use of the whole template sequence. Conditions: 5 nM DNA, 1 mM $MnCl_2$, 5 mM $MgCl_2$, 100 µM NTPs/dNTPs, 30 min at a temperature of 40° C.

FIG. 6 depicts that TthPrimPol is also a RNA-directed polymerase. Shown is the reverse transcription of a RNA template of SEQ ID NO: 12 starting from a DNA primer (SEQ ID NO: 8) The efficiency of the reaction is lower than that reached using a DNA template, and the RNA-instructed DNA polymerase activity seems to strictly depend on manganese. Comparable results were obtained for DNA directed polymerase activity using the same primer and a DNA template (SEQ ID NO: 10). Conditions: 5 nM DNA/RNA, 1 mM $MnCl_2$, 5 mM $MgCl_2$, 1 µM dNTPs, 60 min at a temperature of 40° C.

FIG. 7 depicts the high fidelity of DNA synthesis by TthPrimPol. Each of the four dNTPs was assayed individually as a substrate to be incorporated opposite the four possible templating bases, (template according to SEQ ID NO: 13; primer according to SEQ ID NO: 14) either in the presence of magnesium or manganese ions. In all cases, TthPrimPol preferentially inserts with high fidelity the complementary nucleotide dictated by the first available templating base. Even with manganese, base discrimination during DNA polymerization by TthPrimPol provides high fidelity to form a correct Watson and Crick base pair when extending a correctly paired primer terminus. Conditions: 10 nM DNA, 20 min at a temperature of 40° C., 5 mM $MgCl_2$, 200 nM TthPrimPol, 1 µM dNTPs (upper panel); 1 mM $MnCl_2$, 50 nM TthPrimPol, 100 nM dNTPs (lower panel respectively).

FIG. 8 illustrates comparable affinity of TthPrimPol to its substrate deoxyribonucleotides dTTP, dGTP, dCTP and dATP. Under single turnover conditions, where the enzyme concentration is higher than the concentration of DNA, incorporation of dNTPs clearly reveals that TthPrimPol has a high affinity for dNTPs and no bias towards favoured incorporation of a specific dNTP. Template according to SEQ ID NO: 13; primer according to SEQ ID NO: 14. Conditions: 10 nM DNA, 1 mM $MnCl_2$ 50 nM TthPrimPol, 20 min at a temperature of 40° C.

FIG. 9 depicts TthPrimPol's high tolerance to damaged DNA. The protein was offered templates, according to SEQ ID: 13, containing an abasic site (AP), a 7,8-dihydro-8-oxoadenine (8oxoA), a 7,8-dihydro-8-oxoguanine (8oxoG), a thymine glycol (Tg), a 5-hydroxycytisine (5OHC) or a 5-hydroxyuracil (5OHU). As shown, TthPrimPol is able to perform efficient lesion bypass by template dependent extension of the primer (SEQ ID NO: 14) opposite the lesion, or by skipping the lesion and copying the next template base (dG insertion). Conditions: 10 nM DNA, 1 mM MnCl$_2$, 50 nM TthPrimPol, 100 µM dNTPs, 20 min at a temperature of 40° C.

FIG. 10 depicts efficient bypass of 8oxoG (7,8-dihydro-8-oxoguanine), one of the most frequent forms of damage occurring in DNA as consequence of oxidative stress (Berquist and Wilson 2012), mainly in syn conformation, introducing dATP. Kinetics of dATP insertion opposite the lesion is identical to that opposite undamaged T. Template according to SEQ ID NO:13; primer according to SEQ ID NO:14. Conditions: 10 nM DNA, 1 mM MnCl$_2$, 50 nM TthPrimPol. 20 min at a temperature of 40° C.

FIG. 11 illustrates that TthPrimPol lacks terminal transferase activity as well as exonuclease activity. TthPrimPol is unable to add any nucleotide to the 3' end of homopolymeric ssDNA molecules (SEQ ID NOs 15 and 16), thus suggesting that TthPrimPol is strictly a template-dependent enzyme. Control reactions without dNTPs, also demonstrate that TthPrimPol lacks 3'-5' exonuclease activity, since DNA molecules were not degraded in agreement with the lack of ExoI, ExoII and ExoIII consensus motifs, which form an evolutionarily conserved 3'-5' exonuclease active site in several DNA polymerase families (Bernad, Blanco et al. 1989). Conditions: 5 nM DNA, 400 nM TthPrimPol, 1 mM MnCl$_2$, 5 mM MgCl$_2$ 100 µM dNTPs, 60 min at a temperature of 58° C.

FIG. 12 depicts efficient primer-free amplification of ssDNA by 7TthPrimPol. Both versions of TthPrimPol (+/− His tag) are able to amplify single stranded M13mp18 template DNA in huge amounts in the presence of dNTP substrate, but without addition of specific or random primers, clearly demonstrating TthPrimPol's ability to act as both, DNA primase and DNA polymerase. On the other hand, ribonucleotides (NTPs) seem to be poor substrates for DNA amplification by TthPrimPol. Conditions: 50 mM Tris-HCl pH 7.5, 1 mM DTT, 0.1 µg/µl BSA, 50 mM NaCl, 5% glycerol 1 mM MnCl$_2$, 200 ng M13mp18 ssDNA, 6 h at a temperature of 65° C.

FIG. 13 illustrates that TthPrimPol depends on metal cofactors. Most efficient amplification is detected in the presence of 1 mM Mn$^{2+}$ a) or 5 mM Mg$^{2+}$ b), while Co$^{2+}$ and Ca$^{2+}$ are inappropriate co-factors c) and d) at any tested concentration. Conditions: 50 mM Tris-HCl pH 7.5, 1 mM DTT, 0.1 µg/µl BSA, 32 mM NaCl, 5% glycerol, 200 ng M13mp18 ssDNA 400 nM TthPrimPol. 3 h at a temperature of 65° C.

FIG. 14 depicts that the yield of amplified M13mp11 ssDNA is proportional to the amount of TthPrimPol used in the primer-free assay, either in the presence of Mg$^{2+}$ a) or in the presence of Mn$^{2+}$ b). Conditions: 50 mM Tris-HCl pH 7.5, 1 mM DTT, 0.1 µg/µl BSA, 50 mM NaCl, 5% glycerol, 100 mM dNTPs, 200 ng M13mp18 ssDNA, 400 nM TthPrimPol 3 h at a temperature of 65° C.

FIG. 15 depicts the effect of single stranded template DNA concentration on the yield of amplified DNA. M13mp18 ssDNA in primer free amplification by TthPrimPol. The amount of product is proportional to the initial amount of template DNA, either in the presence of Mg$^{2+}$ (left part) or in the presence of Mn$^{2+}$ (right part). Conditions: 50 mM Tris-HCl pH 7.5, 1 mM DTT, 0.1 µg/µl BSA, 32 mM NaCl, 5% glycerol. 100 µM dNTPs, 400 nM TthPrimPol, 5 mM MgCl$_2$, 1 mM MnCl$_2$, 3 h at a temperature of 65° C.

FIG. 16 illustrates the reaction time dependent yield of amplification product in primer free amplification of M13mp18 ssDNA by TthPrimPol in the presence of Mg$^{2+}$ a) and in the presence of Mn$^{2+}$ b). In either case, the amplification is saturated after 4 hours, perhaps due to dNTP deprivation. Conditions: 50 mM Tris-HCl pH 7.5, 1 mM DT, 0.1 µg/µl BSA, 50 mM NaCl, (32 mM when MgCl$_2$ used as cofactor), 5% glycerol, 100 µM dNTPs, 400 nM TthPrimPol, 200 ng M13mp18 ssDNA, 5 mM MgCl$_2$, 1 mM MnCl$_2$, 65° C.

FIG. 17 shows the amplification products variation in amount and mobility as a function of dNTP concentration. The best dNTP concentration for each metal cofactor ranged from 100 µM when using manganese to 500 µM in the case of magnesium. Higher concentrations seem to be inhibitory. The amplified products in the presence of Mg$^{2+}$ (left part) and Mn$^{2+}$ respectively (right part) had similar mobilities and yield considering the effective intervals of dNTP for each metal. Conditions: 50 mM Tris-HCl pH 7.5, 1 mM DTT, 0.1 µg/µl BSA, 32 mM NaCl, 5% glycerol 400 nM TthPrimPol. 200 ng M13mp18 ssDNA, 5 mM MgCl$_2$. 1 mM MnCl$_2$, 3 h at a temperature of 65° C.

FIG. 18 depicts the effect of incubation temperature with respect to the metal cofactor used in the amplification of ssDNA. The optimal temperature range is broader for manganese (52-62° C.) compared to magnesium (55-60° C.). Conditions: 50 mM Tris-HCl pH 7.5, 1 mM DTT, 0.1 µg/µl BSA, 32 mM NaCl, 5% glycerol 400 nM TthPrimPol 200 ng M13mp18 ssDNA, 100 µM dNTPs, 5 mM MgCl$_2$, 1 mM MnCl$_2$, 3 h.

FIG. 19 illustrates the substitution of random primers by TthPrimPol and subsequent multiple displacement amplification by Phi29 DNA polymerase. The combination of both enzymes is able to proficiently amplify double stranded plasmid DNA. The amount of amplification products increased in a TthPrimPol dose-dependent manner and in the presence of 200 nM TthPrimPol, yield and mobility of the amplified DNA is comparable to the use of random oligonucleotide primers (RP). Conditions: 1 ng pRSET DNA (3 kb), 50 µM random primers (RP), 40 ng Phi29 DNA polymerase, 400 nM TthPrimPol, 10 mM MgCl$_2$, 500 µM dNTPs, 5 h 30° C.

FIG. 20 depicts TthPrimPol dose-dependent rise in amplification products in a series (n=3) of Phi29 whole genome amplification (WGA) experiments. The combination of both enzymes. TthPrimPol and Phi29 DNA polymerase (DNApol), is able to proficiently amplify genomic DNA to yields comparable to the well established WGA method, which 3 uses random primers (RP). Conditions: 650 ng Phi29 DNApol (QualiPhi), 400 nM TthPrimPol, 1 ng genomic DNA, 50 µM random primers, 10 mM MgCl$_2$, 500 µM dNTPs, 16 h 30° C.

FIG. 21 illustrates that TthPrimPol is stable and active over a long period of time. Comparable amount of amplified nucleic acid obtained with the same batch of TthPrimPol enzyme in experiments made on Jul. 7, 2011 and over 19 months later (Mar. 6, 2013). Shown is the primer free amplification of single stranded M13mp18 ssDNA a). Storing TthPrimPol for a period of more than 16 months does not alter its ability to elongate primers in a template dependent manner b). Conditions: for a) 50 mM Tris-HCl pH 7.5, 1 mM DTT. 0.1 µg/µl BSA, 32 mM NaCl, 5% glycerol, 400 nM TthPrimPol, 200 ng M13mp18 ssDNA, 100 µM dNTPs, 3 h 65° C. for b) 5 nM DNA, 5 mM MgCl$_2$ 100 µM dNTPs, 60'40° C., Template and primers according to SEQ ID NOS: 5 and 6.

FIG. 22 depicts that TthPrimPol is a more efficient DNA polymerase than HsPrimPol. Shown is the amplification of M13mp18 ssDNA in the presence of NTPs and dNTPs. Even lower amounts (200 nM) of TthPrimPol produce more amplified nucleic acid than the Hs version. On the other hand, both enzymes utilise NTPs less efficient than dNTPs but in a similar range.

FIG. 23 illustrates that TthPrimPol is able to incorporate fluorescent labelled dNTPs. Shown is the incorporation of Cy5 labelled dCTP. Conditions: 10 nM DNA (SEQ ID NOS: 10 and 8). 100 nM TthPrimPol. 1 mM MnCl$_2$, 5 mM MgCl$_2$, 20 min at a temperature of 40° C.

FIG. 24 depicts an overview of the amino acids and nucleic acids used in the invention.

Figure 25A:
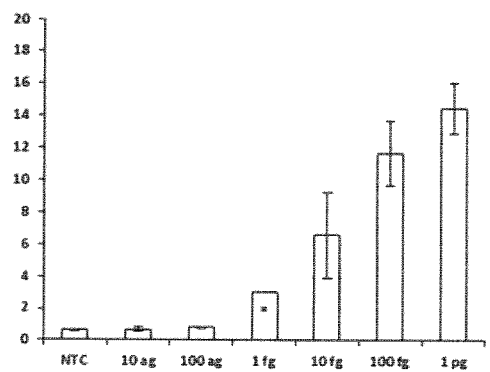
FIG. 25 depicts the minimal amount of template DNA required for its efficient amplification by TthPrimPol in combination with Phi29 DNA polymerase.
Figure 25B:
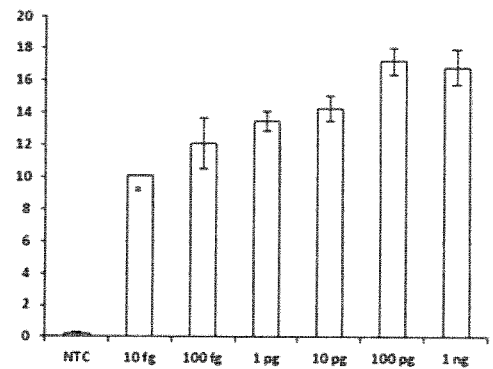

The combination of both enzymes, TthPrimPol and wild-type Phi29 DNA polymerase, is able to proficiently amplify human genomic DNA from at least 10 fg of template DNA. Shown are two independent series (FIG. 25 a and FIG. 25 b) of experiments, each reaction condition is performed in triplicate. The incubation mixtures contained, in 50 µl, 50 mM Tris-HCl pH 7.5, 50 mM KCl, 1 mM DTT. 10 mM MgC2, 500 µM dNTPs, 700 ng wild-type Phi29 DNA pot, 400 nM TthPrimPol and the indicated amounts of human genomic DNA. NTC (non-template control) indicates that no template DNA is added to the reaction. Reaction mixtures were incubated for 6 hours at 30° C. Amplification products were quantified using PicoGreen reagent (Quant-iT™ PicoGreen dsDNA reagent, Invirogen). An asterisk indicates the reactions in which two of the three replicates failed to amplify DNA. X-axis: amount of human genomic template DNA; Y-axis: DNA yield (µg)

Figure 26A:
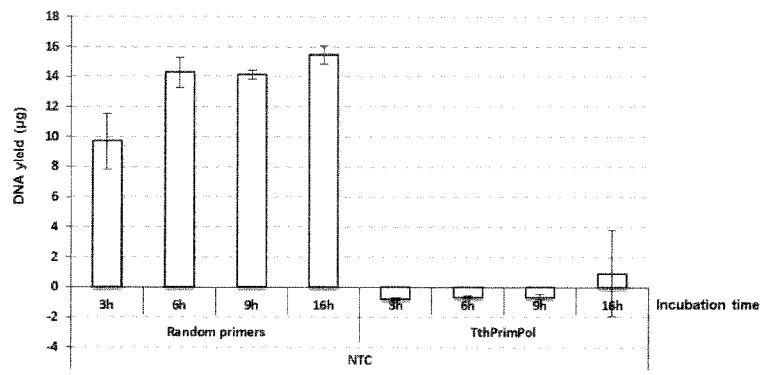
Figure 26B:
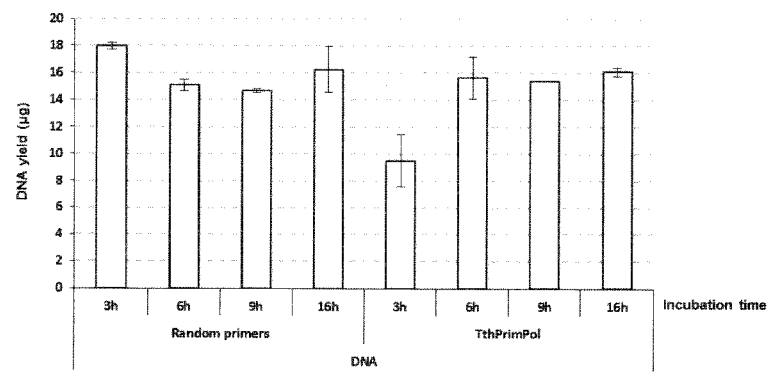

FIG. 26 depicts the suppression of unspecific background DNA amplification by the combination of TthPrimPol with Phi29 DNA polymerase.

The combination of both enzymes, TthPrimPol and Phi29 DNA polymerase, do not produce DNA amplification in the absence of externally added template DNA molecules (FIG. 26 a), in any of the incubation times tested (up to 16 hours). On the other hand, the combination of Phi29 DNA polymerase with random primers gives rise to significant DNA yields even when the reaction is incubated only 3 hours. Therefore, the use of TthPrimPol prevents unspecific background DNA amplification in the absence of externally added template DNA. In Contrast, the combination of both enzymes, TthPrimPol and Phi29 DNA polymerase, do produce comparable amounts of amplified DNA in the presence of externally added template DNA molecules (FIG. 26 b).

Each reaction condition is performed in triplicate. The incubation mixtures contained, in 50 µl, 50 mM Tris-HCl pH 7.5, 50 mM KCl, 1 mM DTT, 10 mM MgCl$_2$, 500 µM dNTPs, 700 ng QualiPhi Phi29 DNA pol (improved version of the enzyme), 400 nM TthPrimPol or 50 µM random primers. NTC (non-template control) indicates that no template DNA is externally added to the reaction. DNA indicates that 1 ng of human genomic DNA is added as template to the reaction. Reaction mixtures were incubated for the indicated hours at 30° C. Amplification products were quantified using PicoGreen reagent (Quant-iT™ PicoGreen dsDNA reagent. Invitrogen).

Figures 27, 28:
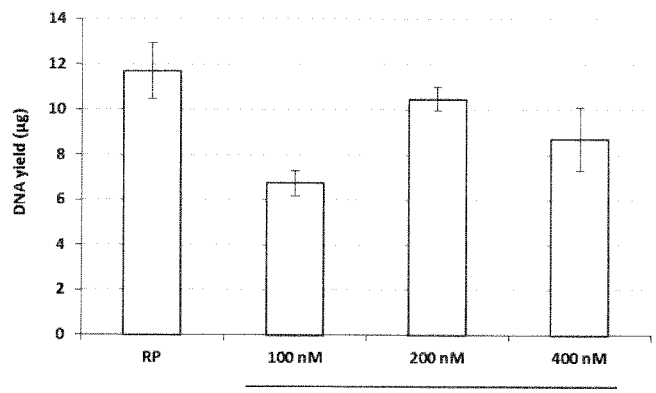

FIG. 27 depicts amplification of yeast genomic DNA by TthPrimPol in combination with Phi29 DNA polymerase. The combination of both enzymes, TthPrimPol and Phi29 DNA polymerase, is able to proficiently amplify yeast genomic DNA to yields comparable to the well-established WGA method, which uses random primers (RP).

The incubation mixtures contained, in 50 µL 50 mM Tris-HCl pH 7.5, 50 mM KC. 1 mM DTT. 10 mM MgCl$_2$, 500 µM dNTPs, 1 ng *Saccharomyces cerevisiae* genomic DNA, 750 ng wild-type Phi29 DNA pol (Repli-G single cell version, Qiagen), 50 µM random hexamers or the indicated amount of TthPrimPol. Reaction mixtures were incubated for 3 hours at 30° C. Amplification products were quantified using PicoGreen reagent (Quant-iT™ PicoGreen dsDNA reagent, Invitrogen).

FIG. 28 shows to which extend the obtained MiSeq sequence reads map to the reference genome. This summary illustrates in detail the total amount of reads for each sample, the amount of reads that mapped to the genome and the amount of reads that didn't map to the reference genome. It further depicts per sample fraction of mapping and not mapping reads, the average read length after quality clipping, as well as the total amount and fractions of bases that mapped or didn't map to the genome.

Most remarkable is the finding that non-amplified samples and Tth/Phi amplified samples map to the same extend (>90%) while only 83.92% of the random primed samples (RP) map on the reference.

FIG. 29 illustrates an over- and underepresentation analysis of signatures on the basis of individual chromosomes. Comparing both, random primed samples (RP) and Tth/Phi amplified samples to non-amplified samples (NA) reveals that the relative difference decreased by 17% from NA samples to Tth/Phi samples.

DETAILED DESCRIPTION OF THE PREFERRED EMBODIMENTS

The various aspects of present invention are described herein below and are defined in the claims.

The hypothetical conserved protein AAS81004.1 from *Thermsus thermophilus* HB27, predicted to contain a primase-polymerase (PrimPol) domain of the type found in bifunctional replicases from archaeal plasmids, including ORF904 protein of the crenarchaeal plasmid pRN1 from *Sulfolobus islandicus* (pRN1 primpol), was cloned, overexpressed in *E. coli* in a soluble and active form, and purified to homogeneity.

The inventors have found that purified TthPrimPol displayed a strong DNA primase activity on a single-stranded oligonucleotide in which a potential primase recognition sequence (GTCC) is flanked by thymine residues (Cavanaugh and Kuchta 2009). Such a tract of pyrimidines has been shown to be the preferred template context for initiation of the priming reaction by several viral, prokaryotic and eukaryotic RNA primases (Holmes. Cheristhundam et al. 1985; Parker and Cheng 1987; Frick and Richardson 2001). Surprisingly, the inventors have found that priming occurred only in front of the "TC" sequence, and that there was no priming opposite the poly dT tracks. Further analysis of template sequence requirements revealed an effect of the nucleotide preceding the template initiation site on TthPrimPol's primase activity—C is preferred over A, G or T. Even if TthPrimPol prefers CTC as template initiation site, it is in general able to act as a primase on any sequence of the generic form XTC, where X stands for either of A, C, G, or T. The modest sequence requirement forms an excellent basis for random priming of nearly all natural templates.

The inventors have further found that TthPrimPol possessed DNA-dependent DNA polymerase activity, which is also known from other AEP primases which are able to carry out the initiation and extension of both RNA and DNA chains of up to 1 kb or 7 kb, respectively (Chemnitz Galal, Pan et at 2012 Lao-Sirieix and Bell 2004; Lao-Sirieix, Pellegrini et at 2005). In addition, the inventors have found that TthPrimPol was able to reverse transcribe RNA into DNA, thus can act as Reverse Transcriptase, and possesses strand displacement activity, when acting on gapped templates. However, in the case of RNA polymerization TthPrimPol is strictly depending on manganese as metal cofactor and less efficient.

These findings gave a first hint about TthPrimPol's ability to utilize a variety of templates as well as substrates. Consequently, the inventors tested TthPrimPol's tolerance to damaged DNA. The protein was offered templates containing an abasic site (AP), a 7,8-dihydro-8-oxoadenine (8oxoA), a 7,8-dihydro-8-oxoguanine (8oxoG), a thymine glycol (Tg), a 5-hydroxycytisine (5OHC) or a 5-hydroxyuracil (5OHU). The inventors surprisingly found that TthPrimPol was able to perform efficient lesion bypass by inserting nucleotides opposite the lesion, or by skipping the lesion and copying the next template base. 8oxoG, one of the most frequent forms of damage occurring in DNA as a consequence of oxidative stress (Berquist and Wilson 2012), was mainly and efficiently bypassed in syn conformation introducing dATP.

Further on, the inventors demonstrated that TthPrimPol possesses strong strand displacement activity making it an attractive polymerase for whole genome amplification (WGA), even in primer free environment, or for use in rolling circle amplification (RCA) of covalently closed DNA.

Figure 21A:
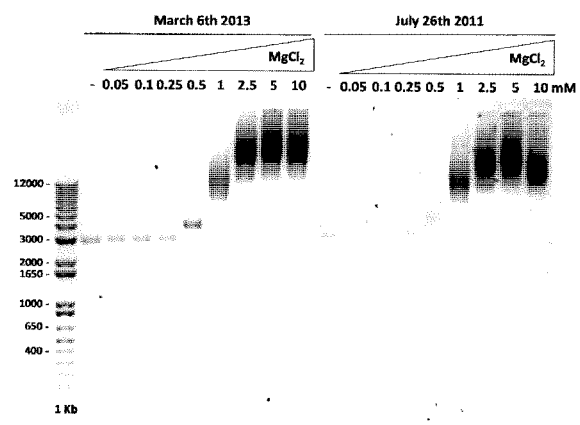
Figure 21B:
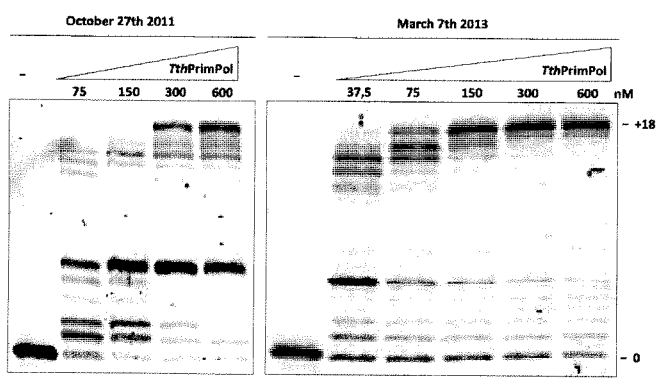

While the above mentioned findings describe the general enzymatic properties of TthPrimPol, technical application of the enzyme in daily laboratory use also depends on basic protein properties like solubility and stability. Unlike the HsPrimPol which looses at least its primase activity shortly after isolation, which might be due to the more complex structure which includes a zinc finger domain close to its C-terminal end (Garcia Gómez, Martinez Jiménez et al. 2012), the inventors found that the zinc finger-free TthPrimPol is highly stable and retains primase and polymerase activity over a long period of time. Surprisingly, the inventors found that neither primase nor polymerase activity of TthPrimPol declines significantly when stored for over 20 months at −80° C. (FIG. 21), making it an attractive protein for the development of reliable methods for all day laboratory use.

These and the other findings herein allow for the development of new, preferably primer-free, reliable methods for amplification, replication, and sequencing of nucleic acids. In further aspects, these findings also allow for the development of new methods for random mutagenesis.

Accordingly, in a first aspect, the present invention relates to a method for replicating, amplifying or sequencing of nucleic acids comprising the following steps
a. providing
  i. a polymerase, or
  ii. a polymerase conjugate,
    wherein the polymerase, or the polymerase moiety of the polymerase conjugate having a sequence that is at least 70% identical to SEQ ID NO: 1 and further comprises polymerase and primase activity, and
b. providing a template nucleic acid, and
c. providing nucleotides and/or nucleotide analogues for incorporation in a complementary strand of nucleic acids, and
d. providing a suitable buffer, and
e. optionally providing one or more primers, and
f. contacting the materials of steps a-e for a suitable amount of time, optionally at high temperature.

In a preferred embodiment, the present invention relates to a method for replicating, amplifying or sequencing of DNA in the absence of a primer comprising the following steps
a) providing
  i) a polymerase, or
  ii) a polymerase conjugate,
  wherein the polymerase, or the polymerase moiety of the polymerase conjugate having a sequence that is at least 70% identical to SEQ ID NO: 1 and further comprises polymerase and primase activity, and
b) providing a template nucleic acid, and
c) providing nucleotides and/or nucleotide derivatives for incorporation in a complementary strand of nucleic acids, and
d) providing a suitable buffer,
e) providing a second polymerase, and
f) contacting the materials of steps a-e for a suitable amount of time.

The terms replicating, amplifying, sequencing, polymerase or "polymerase activity", as well as primer or nucleic acid are well known in the art.

The term nucleic acid for example, is the overall name for DNA and RNA, and is synonymous with polynucleotide. Nucleic acid is found in abundance in all living things, where it functions in encoding, transmitting and expressing genetic information, the basis of inheritance.

For example, the term DNA polymerase activity is designated to the activity of an enzyme that catalyzes the polymerization of deoxyribonucleotides into a DNA strand. DNA polymerase enzymes are best-known for their role in DNA replication, the process of copying a DNA strand, in which a polymerase "reads" an intact DNA strand as a template and uses it to synthesize the new strand. Polymerase activity may be measured for example in an assay according to Example 1) or any of the DNA polymerase activity assays well known to the skilled reader.

In general, the term amplification refers to one of the many ways in which a gene can be overexpressed. As used herein, the term amplification mainly refers to one of the many in-vitro methods in which a piece of DNA, or a whole DNA molecule, can be copied or multiplied. Non limiting examples for in-vitro amplification methods include PCR (Polymerase Chain Reaction). LAMP (Loop mediated Isothermal Amplification), RDC (Reaction déplacement chimeric), NASBA or isothermal amplification with Phi29 polymerase. (U.S. Pat. No. 5,001,050; WO/2011/000997) which are mainly performed as strand displacement amplifications like f.e. rolling circle amplification (RCA) in the case of covalently closed DNA, or whole genome amplification (WGA) of linear genomic DNA.

Due to its thermo stability, and strand displacement capacity, TthPrimPol can beneficial be used in isothermal conditions which require strong strand displacement capacities, as well as in PCR methods. In both cases, the methods of the invention will add a benefit to conventional amplification methods, a TthPrimPol allows re-initiation of the replication fork, which is particularly useful when amplifying damaged DNA.

The term DNA sequencing defines the process of determining the precise order of nucleotides within a DNA molecule, including any method or technology that is used to determine the order of the four bases—adenine, guanine, cytosine, and thymine in a strand of DNA. As of today, a number of different sequencing techniques exist, that are commonly subsummized under first generation sequencing, second generation sequencing, and third generation, or single molecule sequencing (SMS). First generation sequencing refers mainly to the methods of Maxam and Gilbert (Maxam and Gilbert 1977) or Sanger (Sanger. Nicklen et al. 1977; Sanger and Coulson 1978), of which only the latter is used today.

Second, or next generation sequencing refers to techniques that produce many sequences at the same time using advanced technical (optical) detection methods of base positions. An overview over existing methods is given in (Metzker 2009).

NGS technologies are cycle sequencing techniques, also called sequencing by synthesis techniques: Illumina Platform (Bentley, Balasubramanian et al. 2008), Life technologies Ion Torrent platform (www.iontorrent.com/technology-scalability-simplicity-speed). One of the oldest next generation sequencing techniques is pyrosequencing (Ronaghi, Karamohamed et al. 1996; Ronaghi, Uhlen et al. 1998). This technique is based on the detection of pyrophosphate (PPi) that is released during strand extension. Visible light is generated proportional to the number of incorporated nucleotides. The released PPi is converted to ATP by ATP sulfurylase. ATP then provides energy to luciferase to oxidize luciferin and generate a light flash. The DNA sequence can be determined because nucleotides are added in a sequential predetermined order.

Fluorescently modified nucleotides that are used in sequencing applications often pose problems to the utilized polymerases as they do not behave lie the natural substrates for the enzyme. These nucleotides have to be incorporated into the growing strand with high specificity, the fluorescent moiety be cleaved off efficiently following imaging, and be extended efficiently in the next cycle. In cycle sequencing techniques, incorporation of one modified nucleotide results in reversible termination of the reaction, and the modified nucleotide is therefore classified as a "reversible terminator". Two groups of reversible terminators exist: 3'-blocked terminators, with a cleavable group bound to the 3'-oxygen of the 2'-deoxyribose sugar, and 3'-unblocked terminators. Possible blocking groups include 3'-O-allyl (e.g. f 3'-O-allyl-dCTP-allyl-bodipy-FL-510 [$\lambda$ab(max)=502 nm; $\lambda$em (max)=510 nm], 3'-O-allyl-dUTP-allyl-R6G [$\lambda$abs(max)= 525 nm; $\lambda$em(max)=550 nm], 3'-O-allyl-dATP-allyl-ROX [$\lambda$abs(max)=585 nm; $\lambda$em(max)=602 n] 3'-O-allyl-dGTP-allyl-bodipy-650 [abs(max)=630 nm; $\lambda$em(max)=650 nm] (Ju, Kim et al. 2006), used now by Intelligent Biosystem/Qiagen (www.intelligentbiosyssems.com). Another blocking group used is 3'-Oazidomethyl (Bentley, Balasubramanian et al. 2008; Guo. Xu et al. 2008), used by Illumina. Examples of these nucleotides include: ddCTP-N3-Bodipy-FL-510 ($\lambda$abs (max)=502 nm; $\lambda$em (max)=510 nm), ddUTP-N3-R6G ($\lambda$abs (max)=525 nm; $\lambda$em (max) =550 nm), ddATP-N3-ROX ($\lambda$abs(max)=585 nm; $\lambda$em (max)=602 nm), and ddGTP-N3-Cy5 ($\lambda$abs (max)=649 nm; $\lambda$em (max)=670 nm). Attaching a larger group to the 3' end of nucleotides is a disadvantage for incorporation of these nucleotides in comparison to the unmodified substrates. Common solutions for this problem are mutated DNA-polymerases that tolerate the 3'-blocked terminator nucleotides better.

3'-unblocked reversible terminators pose less problems with the polymerase, and often can have similar incorporation characteristics as natural substrates (Wu, Stupi et al. 2007) These nucleotides are N6-alkylated and photocleavable.

Recently, an even more favourable chemistry has been introduced that possibly improves accuracy and read-lengths (Litosh. Wu et al. 2011). This terminator modification is based on 5-hydroxymethyl-2'-deoxyuridine triphosphate (HOMedUTP).

Other 3'-unblocked terminators use steric hindrance of the large dye group to inhibit incorporating additional nucleotides after a first modified nucleotide has been incorporated (Turcatti, Romieu et al. 2008).

In a specific embodiment of the first aspect of the invention, TthPrimPol will favourably be used in Next Generation Sequencing, for which it is well suited because of its high processivity, and its insensitivity to template DNA-modifications, and its high tolerance towards the nucleotides used.

Single molecule sequencing techniques rely on nucleotides where the fluorophore is attached to the terminal phosphate and not the nucleobase (Life Technologies/Visi-Gen and Pacific Biosciences (Eid, Fehr et al. 2009)) and where incorporation by the polymerase is not a big problem and natural bases are incorporated into the growing DNA strand.

Third generation or single molecule sequencing (SMS) techniques do not require prior amplification, and sequence not clones or ensembles of DNA, but single molecules, often in "real time", meaning the online recording of the activity of a polymerase (Sam, Lipson et al. 2011; Thompson and Milos 2011).

Important SMS sequencing platforms include Life Technologies FRET-based technology, that uses quantum dots linked to the polymerase Pacific Biosciences, that uses Phi29 DNApol immobilized at the centre of a Zero-mode waveguide device that measures approximation of fluorescently coupled nucleotides, or Helicos Biosciences, where a primer is immobilized to the glass surface.

A radically different technique is based on 'nanopores' that allow transition of DNA or nucleotides through a membrane (Branton, Deamer et al. 2008). This technology is mainly marketed by Oxford Nanopore Technologies (www.nanoporetech.com). While the initial idea was based on threading a single DNA strand through the pore during synthesis and measuring changes in the ion current through the pore (Maglia, Restrepo at al 2008), another possibility involves using an exonuclease and detecting released nucleotide transition through the pore (Clarke. Wu et al. 2009). This technique could revolutionize pricing for sequencing, as expensive fluorescently labeled nucleotides are no longer necessary.

Proteins used for these nanopores include alpha-hemolysin (Maglia, Restrepo et al. 2008; Jetha, Wiggin et al. 2009) or MspA (Derrington, Butler et al. 2010; Manrao. Derrington et al. 2011; Manrao, Derrington et al. 2012; Pavlenok, Derrington et al. 2012; Butler, Pavlenok et al. 2008).

So far. Phi29 DNApol is mainly used in the applications as described by Lieberman, Manrao or Wendell (Lieberman, Cherf et al. 2010; Manrao, Derrington et al. 2012; Wendell, Jing et al. 2009). In another specific embodiment of the first aspect of the invention. TthPrimPol is used in conjunction or covalently linked to alpha-hemolysin or MspA or similar proteins to improve single molecule nanopore sequencing. One particular advantage of using TthPrimPol in this embodiment is the high tolerance for different nucleotides in the reaction (e.g. dNTPs, NTPs, oxoNTPs). As most applications use differently modified nucleotides (e.g. fluorescent labelled), TthPrimPol is likely to provide higher processivity and quality with modified nucleotides.

Enzymes are complex protein biomolecules with specific biological function. Intact proteins have a primary, secondary, tertiary and sometimes even a quaternary structure.

It is known to the skilled reader, that their biological function and even their molecular stability depends on preservation of these structures and is influenced by a variety of factors like temperature, freeze/thaw cycles, pH, protein concentration, salt conditions, solvents and the like. Moreover, the structure and stability of a protein is even influenced by oxidation of individual amino acids, of which mainly methionine, cysteine, tryptophan, tyrosine and histidine are susceptible to oxidation (Kim. Berry et al. 2001). As used in the art, protein stability is quantitatively described by the standard Gibbs energy change. $\Delta G^0$, involved in unfolding the unique, three dimensional structure to randomly coiled polypeptide chains (Hinz, Steif et al. 1993).

In contrast, as used herein the term stability of a protein or enzyme mainly refers to the preservation of its enzymatic activity over a longer period of time.

As used herein, preservation of enzymatic activity is preferably intended to mean that primase and polymerase activity is preserved by at least 30%, 40%, 50%, preferably by at least 60%, 70%, 80%, preferably by at least 85%, 90%, 95% such as by about 100% of freshly isolated TthPrimPol.

One aspect that influences stability as well as activity of an enzyme is the buffer used for storage and the buffer used for carrying out the enzymatic reaction. Buffers used in the methods of the invention are not limited in particular and persons skilled in the art will routinely be able to optimize buffer conditions for storing, as well as for carrying out the methods of the invention.

A protein for use in any of the methods of the invention is therefore characterized as a protein preserving primase and polymerase activity, as defined herein, over a longer period of time, when stored under suitable conditions. It is known to the skilled reader that stability and therefore shelf life of a protein depends on both the intrinsic nature of the protein and the storage conditions, and variety of methods and techniques are already available in the art to optimize storage conditions. For a comprehensive overview, reference is made to Simpson (Simpson 2005).

In a specific embodiment, the methods of the first aspect of the invention therefore comprise a TthPrimPol enzyme that preferably retains, under suitable storage conditions, its activity for at least over 4, 5, 6 month, preferably for at least 7, 8, 9 month, preferably for at least 10, 11, 12 month, preferably for at least 13, 14, 15 month, preferably for at least 16, 17, 18 month, preferably for at least 19, 20, 21 month, preferably for at least 22, 23, 24 month.

In a most preferred embodiment, the methods of the invention comprise a TthPrimPol enzyme that retains its activity under suitable storage conditions for more than two years.

As used herein, a protein for use in any of the methods of the invention is a protein having a sequence that is at least 70% identical to SEQ ID NO: 1, such as 71%, 72%, 73%, 74%, 75%, 76%, 78%, 79%, 80%, 81%, 82%, 83%, 84%, 85%, 86%, 87%, 88%, 89%, 90%, 91%, 92%, 93%, 94%, 95%, 96%, 97%, 93%, 99% identical to SEQ ID NO: 1, and optionally comprises polymerase and/or primase activity.

In a most preferred embodiment, the protein for use in any of the methods of the invention is a protein having the sequence of SEQ ID NO: 1.

Percentages identity can easily be determined by the skilled person. As a non-limiting example, for a peptide of 20 amino acids, 70% identity to said sequence according to the first aspect means that 14 out of 20 amino acids are identical. In addition, most major biological information hosting web sites, like for example the NCBI or the EBI, offer services for the calculation of identity and/or homology of amino acid sequences as well as for the calculation of identity and/or homology of nucleic acid sequences. A person skilled in the art will know that for example the popular BLAST (Basic Local Alignment Search Tool) software is suitable for such calculations (Altschul, Gish et al. 1990).

It will be understood by a person skilled in the art that the protein for use in any of the methods of the invention, as defined herein, might be a derivative of the protein having SEQ ID NO: 1 and might comprise one or multiple amino acid exchanges, and/or insertions of one or multiple consecutive amino acids, and/or inversions of consecutive amino acids, and/or deletions of amino acids. The protein derivatives for use in any of the methods of the invention may further comprise one or more covalent modifications, which are well known to the skilled person and are not particularly limited. Preferably, said one or more covalent modification(s) are selected from the group consisting of acetylation, amidation, disulfide bond formation, formylation, glycosylation, methylation, phosphorylation, sulfatation.

Generally, the protein or protein derivative for use in any of the methods of the invention may be a chimeric protein, chimeric protein derivative or chimeric protein conjugate. Chimeric peptides etc. are not particularly limited and are generally well-known to the skilled person.

Preferably, such a chimeric protein or chimeric protein derivative is a protein conjugate that comprises a protein or a protein derivative for use in any of the methods of the invention and as disclosed above. As used herein, a "protein conjugate" preferably refers to a conjugate that comprises a protein or protein derivative disclosed herein as well as an additional moiety. Said additional moiety is not particularly limited. Preferably, the additional moiety is covalently bound to a protein or protein derivative disclosed herein. Said additional moiety, for use in methods of the invention, may also refer to more than one such moiety. Accordingly, a protein conjugate may also comprise more than one such moiety, such as two or more moieties of a given type of moieties and/or two or more moieties of different types of moieties. Said moieties are preferably selected from moieties known to interact with nucleic acids such as Helix-Hairpin-Helix moieties, DNA unwinding moieties such as gyrase moieties, or single strand binding moieties such as moieties of E. coli's PriB protein or moieties of icp8 of Herpes simplex.

In general it will be understood by a person skilled in the art that such derivatives or conjugates thereof might possess increased primase and/or polymerase activity compared to the protein activity of a protein having SEQ ID NO: 1, such as an increase by at least 10%, at least 20%, a least 30%, at least 40%, at least 50%, at least 60%, at least 70%, at least 80%, at least 90%, at least 100%, at least 150%, or at least 200%.

In accordance with the invention, a protein, protein derivative, or a conjugate, for use in any of the methods of the invention, might therefore comprise a detectable label or tags that easy the isolation of the protein, protein derivative or conjugate thereof, like for example a His-tag as present in the molecule having SEQ ID NO: 2.

Such protein derivatives or protein conjugates are easily obtainable by a person skilled in the art—e.g. by methods involving chemical synthesis, production in host cells, or combinations thereof.

A long-standing problem in molecular biology is the transcription of RNA into DNA (reverse transcription). This is needed for the construction of cDNA libraries, for PCR-based analyses etc. Up to now, this reverse transcription is done with a number of possible enzymes, e.g. MMLV RT, AMV RT, HIV-1 RT, originally isolated from retroviruses. One problem of RTs so far has been the non-uniform transcription of whole cell mRNA because of complicating secondary structures that can't be melted during the normal reaction temperature of those enzymes (37 or 42° C.). This is especially a problem when trying to reverse transcribe mRNA containing hairpin structures like miRNA.

Several more thermostable version of RT enzymes have been introduced: Mutants of MMLV-RT (Gerard, Fox et al. 1997) (Maxima Reverse Transcriptase, a mutant MMLV RT (www.thermosmietificbio.com/rerse-transcription-rtpcr-rtqper/maxima-everse-transcriptase/by Thermo Scientific), RocketScript™ RT, a mutant MMLV RT that is claimed to work at 70° C. (us.bioneer.com/products/accupower/accu-power-rocketscript-overview.aspx by Bioneer), PyroPhage RT (www.lucigen.com) (Schoenfeld, Patterson et al. 2008; Schoenfeld, Liles et al. 2009; Moser, DiFrancesco et al. 2012), Tth Reverse Transcriptase/DNA Polymerase (*Thermus thermophilus* (Tth) Pol I that in the presence of manganese ions can also transcribe RNA, but is highly inaccurate) (Myers and Gelfand 1991).

TthPrimPol is providing an excellent solution for the problem of reverse transcribing complicated RNA, as it has high thermostability and high processivity.

Therefore, in one preferred embodiment of the current invention, TthPrimPol will be used as an RT with the appropriate buffer.

In an extension of the above, TthPrimPol will also be used as an RT and DNA-Polymerase at the same time in a PCR reaction. The advantages are that RNA can be directly used as template, avoiding the added labour and costs of two separate reactions, and avoiding possible bias and contaminations by two separate reactions. As known to the experts, typical temperature profiles could be used for such a combined reaction (e.g. initial denaturation at 94° C., RT reaction at 70° C. for 30 min, and additional cycling between 94, 50, and 70° C. for the PCR reaction).

As used herein, ther term nucleotides or nucleotide analogues is not limited in particular, and is meant to include deoxynucleoside triphosphates (dNTPs) such as for example, but not limited to dATP, dCTP, dGTP, dTTp, dITP, dUTP or derivatives thereof. As non limiting examples of such derivatives reference is made to dideoxynucleotides such as ddATP, ddCTP, ddGTP, ddTTp, ddITP, ddUTP, or oxidized derivatives like 8oxoA, 8oxoG, 5OHC, 5OHU, or labelled derivatives like fluorescent labelled derivatives or even more complex labels like the labelled used for third generation sequencing.

As used herein, the terms difficult template, damaged DNA, damaged nucleic acid or tainted DNA are used in a mutually interchangeable manner, and refer to nucleic acids comprising alterations in its nucleotide bases that are difficult to deal with with conventional amplification or sequencing methods. As non limiting examples reference is made to physiologically occurring alterations like for example alterations introduced by oxidative stress like f.e. 8oxoA, 8oxoG, or alterations introduced by f.e. crosslinking agents like formaldehyde.

As TthPrimPol is highly acceptant of different DNA-modifications, further embodiments of the first aspect of the invention comprise TthPrimPol for sequencing or amplifying such damaged DNA.

One great demand in the field is sequencing FFPE samples, as many clinical specimens are stored in such a form. Crosslinking agents such as formaldehyde or paraformaldehyde can introduce alterations in the DNA that re difficult to deal with with conventional approaches. Consequently, in a specific embodiment the method of sequencing or amplifying nucleic acids is a method that comprises DNA or RNA template from samples of FFPE specimens.

In a further specific embodiment the method of sequencing or amplifying nucleic acids is a method that comprises oxidized nucleotide bases like for example 8oxoA, 8oxoG, 5OHC, 5OHU.

Likewise, due to the high tolerance in template composition TthPrimPol can be used to amplify and sequence forensic DNA material, or DNA from archaeological samples.

In another embodiment, TthPrimPol can be used to decipher DNA-modifications that occur physiologically. Examples of such modifications are: 8oxoA, 8oxoG, 5OHC, 5OHU. As characterized by the example on 8oxoG, TthPrimPol can "read" the modification by inserting nucleotides with a certain probability into the synthesized strand. In the case of 8oxoG, dA will be inserted at least 5 times more frequently than dC opposite the lesion sites. Specific characteristic distributions or preferences of insertion exist for the different modifications. When doing deep sequencing, the original DNA modifications at position X can be inferred from the fractional distribution of read nucleotides at this position, since many different reads of the same sequence are obtained (e.g. 30-50 reads). Likewise, for Thymidin-dimers, the DNA modification can be established from base deletions from the original sequence.

This application is advantageous for example in the field of aging, where effects of drugs could be monitored by determining the nature and extent of DNA modifications. Likewise, such applications can be useful in the field of oncology to determine effects of a particular therapy, or stage cancer cells.

Both basic genome research as well as clinical diagnostic applications turn towards the analyses of smaller and smaller samples down to single cells. Likewise, forensic analyses are also dependent on often very small amounts of genetic material. In all these cases it is of extreme importance that no nucleic acid is brought in anywhere in the process from sample taking up to handling and amplification of the genetic information for downstream purposes like sequencing or DNA array hybridization.

One source of contamination that is often difficult to avoid is nucleic acid material that comes with enzyme preparations or reagents (e.g. buffers, nucleotides etc.).

Multiple displacement amplification (MDA) using phi29 polymerase and random hexamer primers has become the preferred method for single cell WGA due to the high fidelity of the Phi29 polymerase and its high processivity (Macaulay I C, Voet T. 2014). However, other less favoured methods also exist that make use of random primers, for example PEP-PCR or DA-PCR based applications such as MALBAC (Zhang L et al. 1992).

For example, Woybe et al. find contamination of bacterial origin in common MDA reagents. Also, Blainey and colleagues (2011) find DNA present in three commercially available Phi29 polymerase preparations using a new sensitive detection method called digital MDA (dMDA). Contamination of Phi29 polymerase by *E. coli* DNA has also been found by Yokouchi and colleagues (Yokouchi H. et at 2006).

Presence of external DNA contamination in PCR type reaction using Taq polymerase or variants thereof has been reported broadly in the literature, e.g. Hein et al., (2007); Corless et at, (2000) and Champlot S. et al. (2010).

Example 15 of the invention describes one implementation of the replacement of random primers with PrimPol to suppress continuation amplifications. The example describes a combination with Phi29 DNA polymerase, other polymerases (e.g. Taq polymerase) could also be used here.

There is an ever increasing need to amplify very small amounts of DNA for downstream analyses. This applies for example to forensic or pathologic specimens, but also to single or few cells. A particularly interesting application is sequencing of such amplified material to obtain for example information on genetic differences between cells in healthy or diseased tissue. In medicine, this is extremely valuable in the field of oncology, where the choice of drugs (e.g. kinase inhibitors) is made based on the mutations identified. It is therefore of extreme importance that the amplified material reflects with maximal fidelity the original sequence features of the sample.

However, the current methodologies for amplifying genetic material from small samples are imperfect. There is bias in the representation of the original nucleic acid material. This has been systematically assessed in a number of scientific publications.

For example, Pinard and colleagues (Pinard et al. 2006) examined different amplification methods including multiple displacement amplification (MDA). There was a significant deviation from the coverage of genomic regions compared to unamplified samples. Also there was a bias on GC content deviating from the unamplified samples.

Also, Paez et al. (2004) reported selective under-representation and loss from amplified nucleic acid material. Raghunathan et at (2005) found bias using a qPCR approach of DNA amplified by MDA from single *E. coli* cells. Moreover, sequence loss related to regional proximity to the ends of both human and yeast chromosomes has also been described (Lage et al. (2003)). Hosono et al. (2003) describes that MDA-type amplification resulted in over- or underrepresentation of genomic loci as judged by qPCR.

Han et al. (2012) found alterations in apparent copy number variations (CNVs) in human DNA amplified by MDA. They found that regions that were consistently under-amplified contained also higher GC-content. Pugh et al. (2008) also identified significant apparent alterations in CNVs in relation to GC content and near chromosome ends.

These artifacts introduced by the MDA process poses a significant problem, especially for clinical uses in diagnostics and therapy decision making. It is clear that at least part of this bias is due to the random primers essentially needed for the MDA process together with Phi29 DNA polymerases as alterations of the type of random primers used modifies the type of bias introduced (Alsmadi et at 2009). Therefore there is a need for an alternative amplification process with less or at least a different type of bias introduced.

Example 16 shows that the substitution of TthPrimPol for random primers in MDA-type amplifications offers such an alternative.

Consequently, in a preferred embodiment, the present invention relates to a method according to the invention, wherein the amplification of contaminant DNA is suppressed.

EXAMPLES

Next, the present invention is further described by reference to the following, non-limiting examples.

Example 1

Particular Materials and Methods

Cloning of TthPrimPol:

Sequence analysis of the *Thermus thermophilus* HB27 genome (DDBJ/EMBL/GeneBank AE017221.1; GI:46197919) revealed the ORF TTC0656, encoding a protein that belongs to the archaeal/eukaryal primase (AEP) superfamily. Using this sequence information, we synthesized two primers (SEQ ID II and 17) for amplification of the TthPrimPol gene by PCR from *Thermus thermophilus* genomic DNA. The gene fragment amplified by PCR using Expand High Fidelity polymerase (Roche) was ligated into the pGEM T-easy vector (Promega) by TA cloning and confirmed by sequencing. Using the NdeI and EcoRI sites, the fragment bearing the target gene was ligated into pET21 and pET28 vectors (Novagen). pET28 vector allows the expression of recombinant proteins as fusions with a multifunctional leader peptide containing a hexahistidyl sequence for purification on $Ni^{2+}$-affinity resins.

Overproduction and purification of TthPrimPol:

Expression of TthPrimPol was carried out in the *Escherichia coli* strain BL21-CodonPlus (DE3)-RIL (Stratagene), with extra copies of the argU, ileY, and leuW tRNA genes. Expression of TthPrimPol was induced by the addition of 1 mM IPTG to 1.5 liters of log phase *E. coli* cells grown at 30° C. in LB to an Abs600 nm of 0.5. After induction, cells were incubated at 30° C. for 5 h. Subsequently, the cultured cells were harvested, and the pelleted cells were weighed and frozen (−20° C.).

TthPrimPol–His Tag Purification:

Just before purification, which was carried out at 4° C., frozen cells (3.7 gr) were thawed and resuspended in 20 ml buffer A (50 mM Tris-HCl, pH 7.5, 5% glycerol, 0.5 mM EDTA, 1 mM DTT) supplemented with 1 M NaCl, and then disrupted by sonication on ice. Cell debris was discarded after a 5-min centrifugation at 3000 rpm. Insoluble material was pelleted by a 20-min centrifugation at 11000 rpm. DNA was precipitated with 0.4% polyethylenimine (10% stock solution in water, pH 7.5) and sedimented by centrifugation for 20 min at 11000 rpm. The supernatant was diluted to a final concentration of 0.25 M NaCl with buffer A and precipitated with ammonium sulphate to 30% saturation to obtain a polyethylaeimine-free protein pellet. This pellet was resuspended in buffer A supplemented with 0.25% Tween-20, and loaded into a HiTrap Heparin HP column (5 ml, GE Healthcare) equilibrated previously in this buffer supplemented with 0.2 M NaCl and 0.25% Tween-20. After exhaustive washing with buffer A supplemented with 0.2 M NaCl and 0.25% Tween-20, proteins were eluted with a linear gradient of 0.2-0.8 M NaCl. The eluate containing TthPrimPol was diluted with buffer A to a final 0.2 M NaCl concentration, and loaded into a monoS 4.6/100 PE column (1.7 ml, GE Healthcare), equilibrated previously in buffer A supplemented with 0.2 M NaCl and 0.25% Tween-20. The column was washed, and the protein eluted with a linear gradient of 0.1-1 M NaCl. Fractions containing TthPrimPol were pooled, diluted to 0.2 M NaCl and loaded into a HiTrap Heparin HP column (5 ml, GE Healthcare) equilibrated previously in the same buffer. The column was washed, and the protein eluted with buffer A supplemented with 1 M NaCl and 0.25% Tween-20. This faction contains highly purified (>99%) TthPrimPol. Protein concentration was estimated by densitometry of Coomassie Blue-stained 10% SDS-polyacrylamide gels, using standards of known concentration. The final fraction, adjusted to 50% (v/v) glycerol, was stored at −80° C.

TtPrimPol+His Tag Purification:

Just before purification, which was carried out at 4° C., frozen cells (3.5 g) were thawed and resuspended in 20 m buffer A (50 mM Tris-HCl, pH 7.5, 5% glycerol 0.5 mM EDTA, 1 mM DTT) supplemented with 1 M NaCl, 0.25% Tween-20 and 30 mM imidazole, and then disrupted by sonication on ice. Cell debris and insoluble material were discarded alter a 50-min centrifugation at 40000 g. The supernatant was loaded into a HisTrap crude FF column (5 ml, GE Healthcare) equilibrated previously in buffer A supplemented with 1 M NaCl, 0.25% Tween-20 and 30 mM imidazole. After exhaustive washing with buffer A supplemented with 1 M NaCl, 0.25% Tween-20 and 30 mM imidazole, proteins were eluted with a linear gradient of 30-250 mM imidazole. The eluate containing TthPrimPol was diluted with buffer A supplemented with 0.25% Tween-20, to a final 0.1 M NaCl concentration, and loaded into a HiTrap Heparin HP column (5 ml, GE Healthcare), equilibrated previously in buffer A supplemented with 0.1 M NaCl and 0.25% Tween-20. The column was washed, and the protein eluted with buffer A supplemented with 1 M NaCl and 0.25% Tween-20. This fraction contains highly purified (>99%) TthPrimPol. Protein concentration was estimated by densitometry of Coomassie Blue-stained 10% SDS-polyacrylamide gels, using standards of known concentration. The final fraction, adjusted to 50% (v/v) glycerol, was stored at −80° C.

DNA Substrates:

Synthetic oligonucleotides purified by PAGE were obtained from Sigma. To evaluate the polymerase activity of TthPrimPol, template/primer molecules were generated by annealing P1 primer (5' CTGCAGCTGATGCGCC; SEQ ID NO: 6) to T1 template (5' GTACCCGGG-GATCCGTACGGCGCATCAGCTGCAG; SEQ ID NO: 5), or P2 primer (5' GTACCCGGGGATCCGTAC; SEQ ID NO: 14) to T2 templates (5' CTGCAGCTGATGCGCXGTACG-GATCCCCGGGTAC; SEQ ID NO: 13), where X is A, C, G, T, abasic site (AP), 7,8-dihydro-8-oxoadenine (8oxoA), 7,8-dihydro-8-oxoadenine (8oxoG), thymine glycol (Tg), 5-hydroxycytisine (5OHC) or 5-hydroxyuracil (5OHU), or P3 primer (5' GATCACAGTGAGTAC; SEQ ID NO: 8) to T3 templates (T3$_{DNA}$, 5' AGAAGTGTATCTTGTACT-CACTGTGATC; SEQ ID NO: 10 or T3$_{RNA}$ 5' AGAAGU-GUAUCUUGUACUCACUGUGAUC; SEQ ID NO: 12). 5-nucleotide gapped molecules were generated by annealing P3 primer (SEQ ID NO: 8) to T4 template (5' ACTGGC-COTCGTTCTATTGTACTCACTGTGATC; SEQ ID NO:7) and to downstream oligonucleotide DG5P (5' AACGACGGCCAGT with a 5'-phosphate group; SEQ ID NO: 9). Primers were fluorescently (Cy5) labelled at their 5'-ends. Each primer was hybridized to template or to template and downstream oligonucleotides to generate different DNA molecules in the presence of 50 mM Tris-HCl, pH 7.5, and 0.3 M NaCl and heating to 80° C. for 10 min before slowly cooling to room temperature over night. To assay primase activity, we used the XTCC oligonucleotide (5'T$_{15}$CCTXT$_{10}$ where X is A, C, G or T; SEQ ID NO: 4), containing a putative herpes virus priming initiation site (Cavanaugh and Kuchta 2009).

Primase Assays:

M13mp18 ssDNA (20 ng/μl) or XTCC oligonucleotide (1 μM) were used as templates to assay primase activity. The reaction mixtures (20 μl) contained 50 mM Tris-HCl pH 7.5, 75 mM NaCl, 5 mM MgCl$_2$ or 1 mM MnCl$_2$, 1 mM DTT, 2.5% glycerol, 0.1 mg/ml BSA, [α-$^{32}$P]dATP (16 nM; 3000 Ci/mmol) or [γ-$^{32}$P]ATP (16 nM; 3000 Ci/mmol), the indicated amounts of each dNTP or NTP, in the presence of TthPrimPol (400 nM). After 60 min at 55° C., reactions were stopped by addition of formamide loading buffer (10 mM EDTA, 95% v/v formamide, 0.3% w/v xylen-cyanol). Reactions were loaded in 8 M urea-containing 20% polyacrylamide sequencing gels. After electrophoresis, de novo synthesized polynucleotides (primers) were detected by autoradiography.

DNA and RNA Polymerization Assays:

The incubation mixtures contained, in 20 μl, 50 mM Tris-HCl pH 7.5, 5 mM MgCl$_2$ or 1 mM MnCl$_2$, 1 mM DTT, 5% glycerol, 0.1 mg/ml BSA, 5 nM of the DNA hybrid indicated in each case, the indicated concentration of each dNTP or NTP, and the indicated amount of TthPrimPol. Reaction mixtures were incubated at 40° C. for the indicated times and stopped by adding 10 μl of stop solution (10 mM EDTA and 97.5% deionized formamide). Extension of the labelled primer strand was analyzed by 8 M urea and 20% PAGE, and visualized using a Typhoon 9410 scanner (GE Healthcare).

Circular DNA Amplification Reactions:

M13mp18 ssDNA and pET28 dsDNA were used as templates to assay the amplification capacities of TthPrimPol. The incubation mixtures contained, in 20 μl, 50 mM Tri-HCl pH 7.5, 1 mM DTT, 5% glycerol, 0.1 mg/ml BSA, the indicated amount of template DNA, the indicated concentration of MgCl$_2$ or MnCl$_2$, the indicated concentration of dNTPs or NTPs, and the indicated amount of TthPrimPol. Reaction mixtures were incubated at different temperatures (ranging from 35 to 85° C.) for the indicated times and stopped by reducing temperature on ice. Amplification products were analysed by native gel electrophoresis.

Random Primer Synthesis for Phi29 DNApol-Based Rolling Circle Amplification (RCA):

The incubation mixtures contained, in 12.5 μl, 40 mM Tris-HCl pH 7.5, 50 mM KCl, 45 mM (NH$_4$)$_2$SO$_4$, 10 mM MgCl$_2$, 0.025% Tween-20, 500 μM dNTPs, 50 μM random hexamers, 1 ng pRSET, 40 ng Phi29 DNApol, and the indicated amount of TthPrimPol. Reaction mixtures were boiled (3 min at 95° C.) to denature template DNA before adding the enzymes. Then, reaction mixtures were incubated for 5 hours at 30° C. Amplification products were digested with HindIII and analysed by native gel electrophoresis.

Random Primer Synthesis for Phi29 DNApol-Based Whole Genome Amplification (WGA):

The incubation mixtures contained, in 50 μl, 40 mM Tris-HCl pH 7.5, 50 mM KCl, 45 mM (NH$_4$)$_2$SO$_4$, 10 mM MgCl$_2$, 0.025% Tween-20, 500 μM dNTPs, 50 μM random hexamers, 1 ng human genomic DNA, 650 ng Phi29 DNApol, and the indicated amount of TthPrimPol. Reaction mixtures were incubated for 16 hours at 30° C. Amplification products were quantified using PicoGreen reagent (Quant-iT™ PicoGreen dsDNA reagent, Invitrogen).

Yeast propagation and isolation of genomic DNA. The yeast strain BY4741 was received from Euroscarf (Institute of Molecular Biosciences J.-W. Goethe-University Frankfurt) and propagated in YPD (10 g Yeast Extract, 20 g Peptone, 20 g Dextrose per liter) medium at 30° C. 50 ml of 2 independent overnight cultures (OD60=1; ~1.5×109 cells) were used for the isolation of genomic DNA following the recommended protocol for Qiagen's genomic Tips 100/G (QIAGEN Genomic DNA Handbook 04/2012).

Isolated DNA was analysed on a 1% agarose gel and OD was measured: OD260/280 and OD260/230. Finally the DNA was tested for digestibility: 100 ng ygDNA were digested with 1U EcoRI for 1 h at 37° C.

Two samples of yeast DNA of a concentration of 200 ng/µl were isolated. Sample #1 was used in downstream experiments.

MiSeq Sequencing of Yeast DNA:

Starting from 2 µg of either non-amplified yeast DNA (sample NA), conventional amplified yeast DNA (sample RP), and yeast DNA amplified by rising amounts of Tth-PromPol (100, 200 and 400 ng respectively) in combination with Phi29 polymerase (sample names Tth-100/Phi, Tth-200/Phi and Tth-400Phi), library preparation, multiplexing and sequencing of the 5 samples, on a MiSeq sequencing machine (Illumina, USA), was done by GATC (GATC Biotech AG, Germany), an authorized service provider for Illumina sequencing. Chosen sequencing parameters are as follows: paired end reads, read length 300 bp. GATC returned the data in 10 fastq files, one for each sample and readdirection.

Example 2

Figure 1:
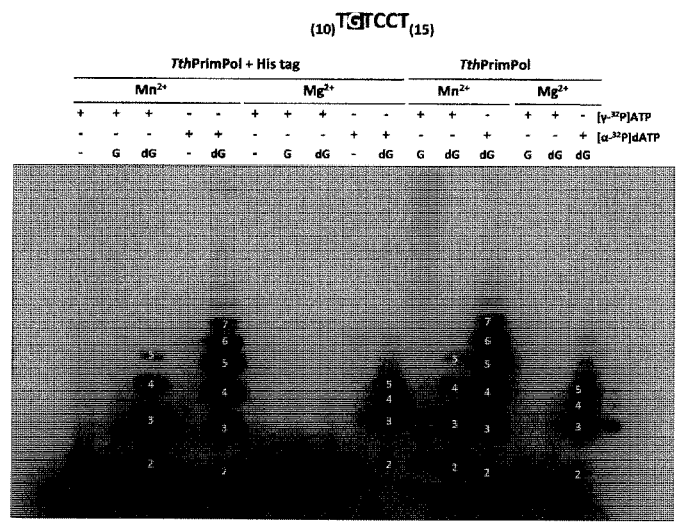
Figure 2:
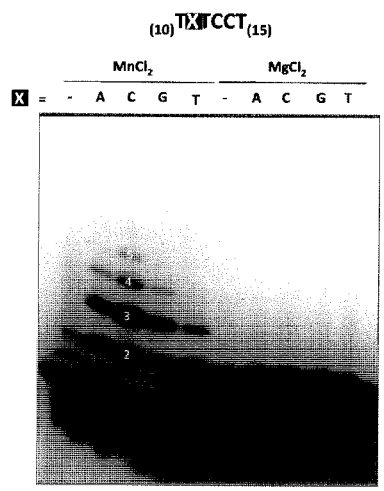

TthPrimPol is an Active Primase that can Initiate Nucleic Acid Synthesis with dNTPs Purified TthPrimPol displayed DNA primase activity on a single-stranded oligonucleotide in which a potential primase recognition sequence (GTCC) is flanked by thymine residues (Cavanaugh and Kuchta 2009). Such a tract of pyrimidines has been shown to be the preferred template context for initiation of the priming reaction by several viral, prokaryotic and eukaryotic RNA primases (Holmes, Cheriathundam at al. 1985; Parker and Cheng 1987; Frick and Richardson 2001). As shown (FIG. 1), priming occurred only in front of the "TC" sequence, and there was no priming opposite the poly dT tracks. The nucleotide acting as the primer (5' position) can be either a ribonucleotide (ATP) or a deoxynucleotide (dATP) in the presence of manganese, but only a deoxynucleotide (dATP) when magnesium was the metal cofactor. Added nucleotides (3' position) must be deoxynucleotides (dGTP), regardless of the metal cofactor. Analysis of template sequence requirements demonstrated the strong effect of the nucleotide preceding the template initiation site. As shown in FIG. 2, TthPrimPol primase activity was maximal when C was the nucleotide preceding the start site. Therefore, TthPrimPol showed preference for CTC as the template initiation site. Moreover, as shown (FIG. 3), TthPrimPol displayed DNA primase activity on a single-stranded circular DNA template (M13mp18 ssDNA). Interestingly, the protein was strictly dependent on deoxynucleotides for synthesis, whereas virtually no products were generated in the presence of ribonucleotides.

In general, primases make RNA primers but the AEP-related primases of Arches and some Bacteria are the exception to this rule (Sanchez-Berrondo, Mesa et al. 2011; Lao-Sirieix, Pellegrini et al. 2005), using dNTPs as valid substrates for priming. This unusual RNA/DNA primase activity was demonstrated to be also inherent to TthPrimPol.

Example 3

TthPrimPol is Also an Efficient Polymerase

Figure 5:
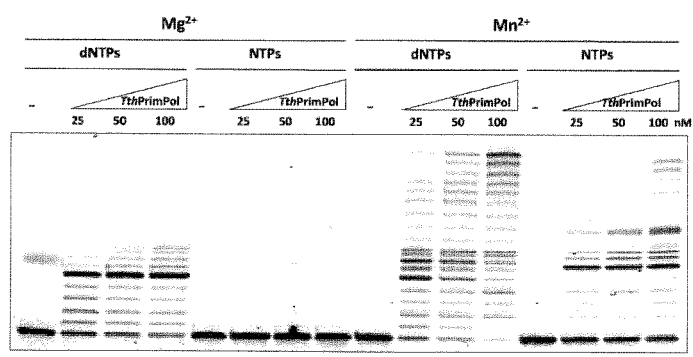

Unlike eukaryotic primases, archeal primases are able to carry out the initiation and extension of both RNA and DNA chains of up to 1 kb or 7 kb, respectively (Chemnitz Galal, Pan et al. 2012; Lao-Sirieix and Bell 2004; Lao-Sirieix, Pellegrini et al. 2005). Therefore, these enzymes are both primases and polymerases, or "PrimPols" (Lipps, Rother et al. 2003). Consequently, we first tested whether, in addition to its DNA/RNA primase activity, TthPrimPol possessed DNA-dependent DNA polymerase activity. As shown in FIG. 4, TthPrimPol was able to completely extend a template/primer molecule by polymerizing up to 18 deoxynucleotides. Magnesium and manganese were valid as metal cofactors for DNA polymerization although manganese was the most efficient metal ion. As shown (FIG. 5), TthPrimPol was also able to perform DNA and RNA synthesis on gapped DNA molecules, while with lower efficiency in the case of RNA polymerization. Moreover, RNA polymerase activity seemed to be strictly dependent on manganese. Additionally, manganese strongly stimulated the strand-displacement synthesis on gapped DNA, allowing the use of the whole template sequence available (+18).

Example 3

TthPrimPol Possesses Reverse Transcriptase Activity

Figure 6:
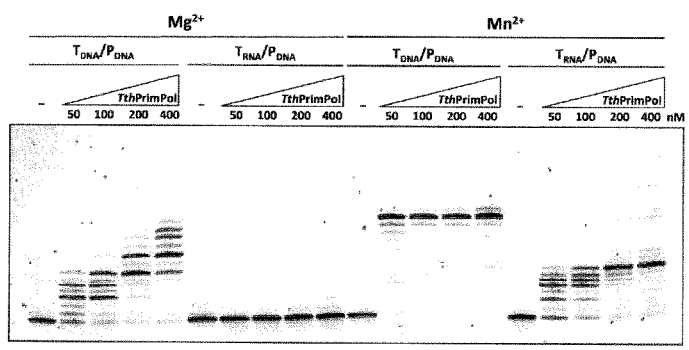

As shown (FIG. 6), TthPrimPol was able to use a RNA template to synthesize the complementary DNA strand, although the efficiency of the reaction was lower than that reached using a DNA template. Moreover, RNA-instructed DNA polymerase activity seemed to be strictly dependent on manganese.

Example 4

TthPrimPol Incorporates dNTPs with Fidelity

Figure 7:
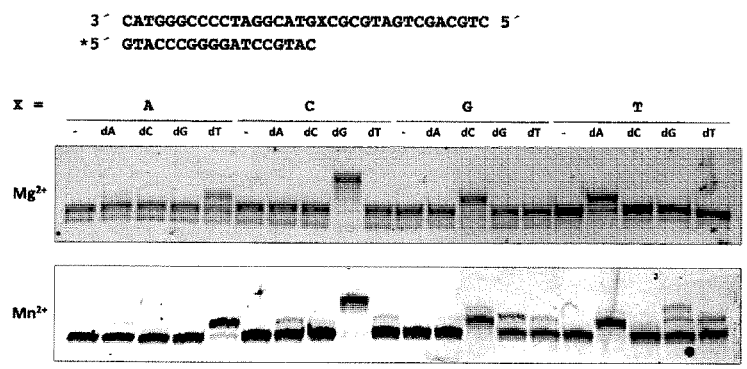
Figure 8:
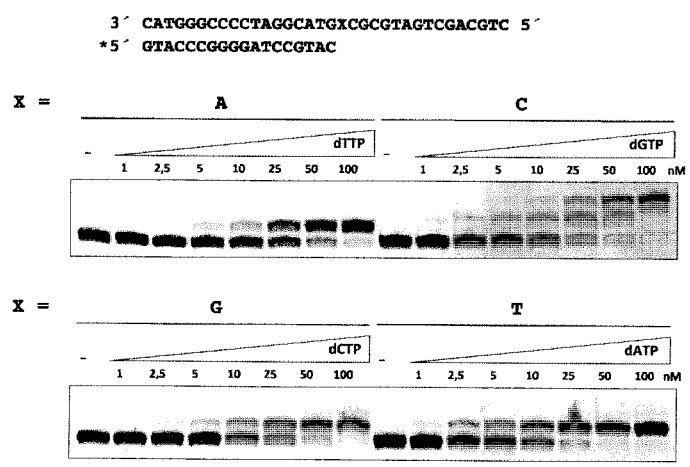

To analyse the capacity of TthPrimPol to catalyse faithful DNA synthesis, each of the four dNTPs was assayed individually as a substrate to be incorporated opposite the four possible templating bases, either in the presence of magnesium or manganese ions. FIG. 7 depicts that in all cases TthPrimPol preferentially inserted the complementary nucleotide dictated by the first available templating base. Even with manganese, base discrimination during DNA polymerization by TthPrimPol provided a strong bias to form a correct Watson and Crick base pair when extending a correctly paired primer terminus. In addition, several assays were performed to determine the TthPrimPol's affinity for dNTPs. Under single turnover conditions, where the enzyme concentration is higher than the concentration of DNA (FIG. 8), dNTP incorporation clearly revealed that TthPrimPol has a high affinity for dNTPs, as the enzyme was able to efficiently insert complementary nucleotides provided at low concentrations.

Example 5

TthPrimPol is Highly Tolerant to Damaged DNA

Figure 9:
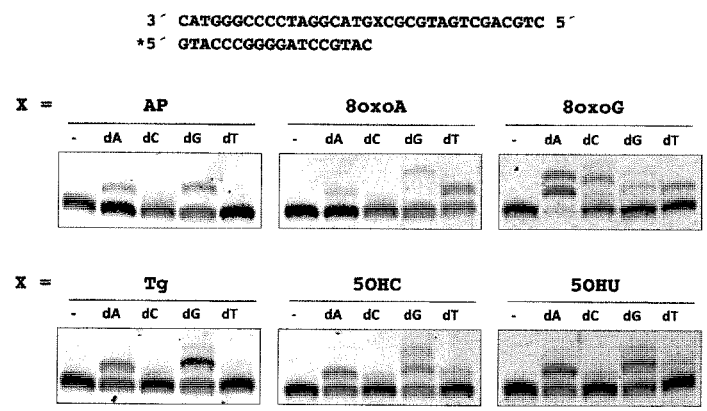
Figure 10:
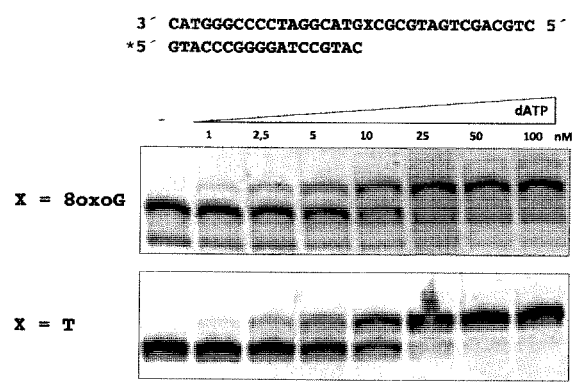

To determine 7TthPrimPol's tolerance to damaged DNA, the protein was offered templates containing an abasic site (AP), a 7,8-dihydro-8-oxoadenine (8oxoA), a 7,8-dihydro-8-oxoguanine (8oxoG), a thymine glycol (Tg), a 5-hydroxycytisine (5OHC) or a 5-hydroxyuracil (5OHU). As shown in FIG. 9, TthPrimPol was able to perform efficient lesion bypass by inserting nucleotides opposite the lesion, or by skipping the lesion and copying the next template base (dG insertion). The oxidized form of guanine (8oxoG), one of the most frequent forms of damage occurring in DNA as a consequence of oxidative stress (Berquist and Wilson 2012), was mainly and efficiently bypassed in syn conformation introducing dATP. As shown (FIG. 10), the kinetics of dATP insertion opposite 8oxoG was identical to that opposite undamaged T.

Figure 11:
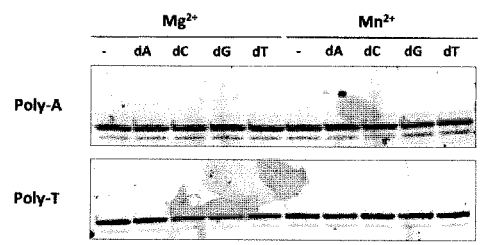

Whereas TthPrimPol was able to perform synthesis on template-primer and gapped DNA molecules, it was unable to add any nucleotide to the 3' end of homopolymeric ssDNA molecules (FIG. 11), thus suggesting that TthPrimPol is strictly a template-dependent enzyme. Control reactions without dNTPs, also demonstrated that TthPrimPol lacks 3'-5' exonuclease activity, since DNA molecules were not degraded, in agreement with the lack of ExoI. ExoII and ExoIII consensus motifs, which form an evolutionarily conserved 3'-5' exonuclease active site in several DNA polymerase families (Bernd, Blanco et al. 1989).

Example 6

TthPrimPol Performs Efficient Circular DNA Amplification

Figure 12:
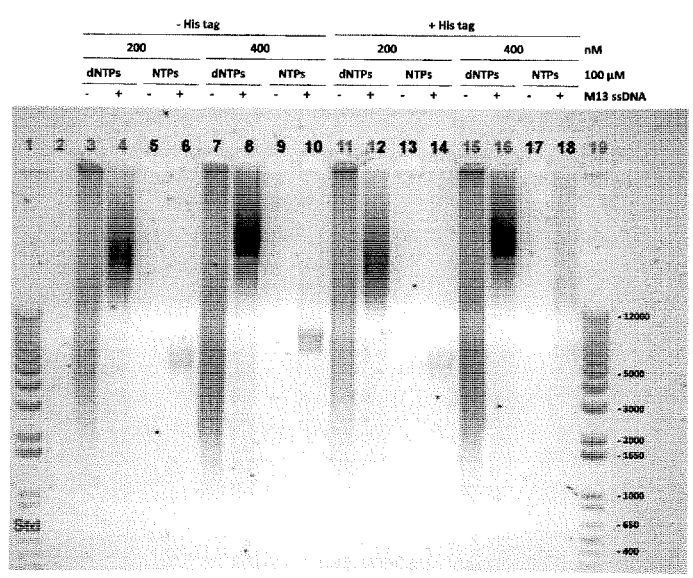
Figure 13A:
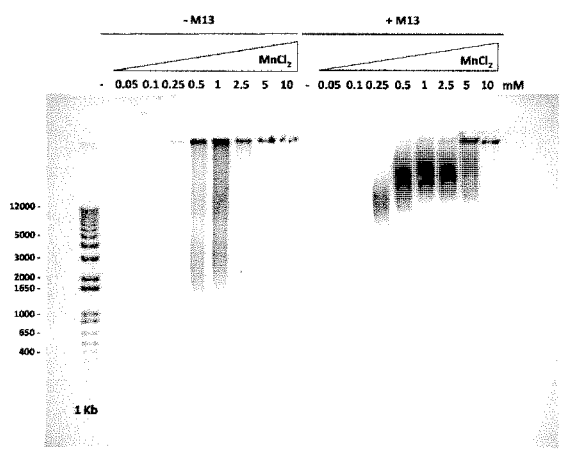
Figure 13B:
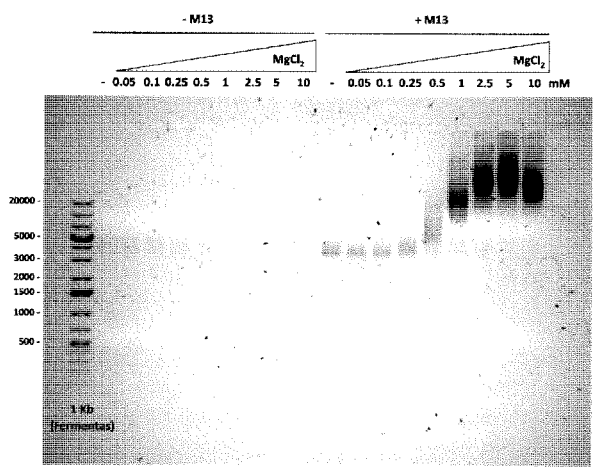
Figure 13C:
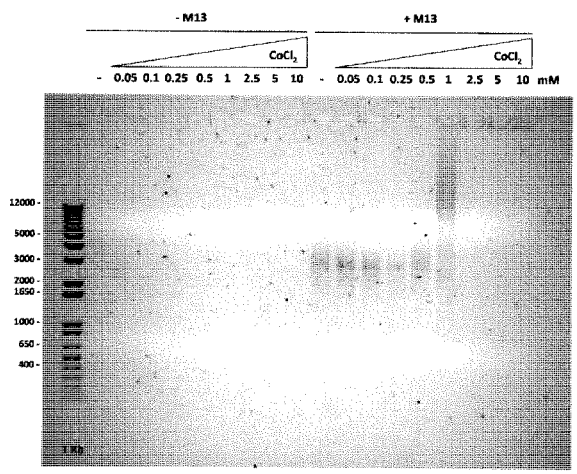
Figure 13D:
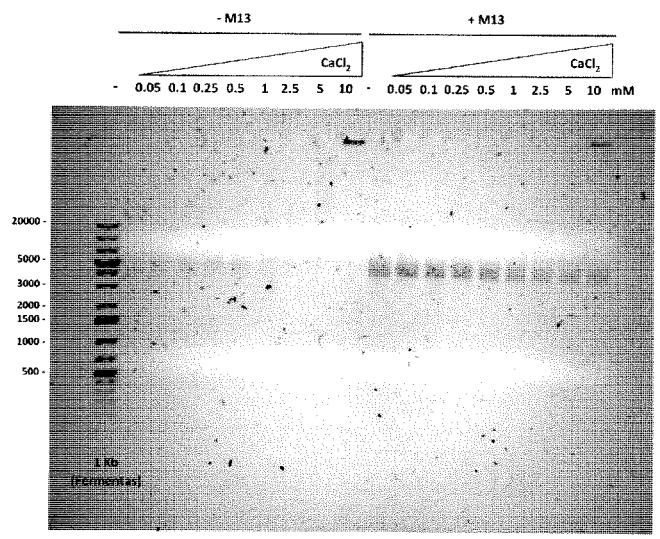

Since TthPrimPol combines highly efficient DNA primase and DNA polymerase activities, we hypothesized that the enzyme could perform DNA amplification proficiently. In order to determine the amplification capacity of TthPrimPol, M13mp18 ssDNA was used as template DNA in the presence of TthPrimPol and dNTPs or NTPs, but in the absence of any specific or random primer. As shown in FIG. 12, both versions of TthPrimPol (+/− His tag) were able to amplify input DNA in huge amounts in the presence of dNTPs. On the other hand, ribonucleotides seemed to be poor substrates for DNA amplification by TthPrimPol.

Example 7

Cofactors

As shown in FIG. 13 a-d, only manganese and magnesium could act as metal cofactors during amplification reactions, whereas cobalt and calcium were not useful as activating metal ions. The amount of amplification products was maximal at concentration intervals 0.5-2.5 mM for manganese, and 2.5-10 mM for magnesium.

Figure 14A:
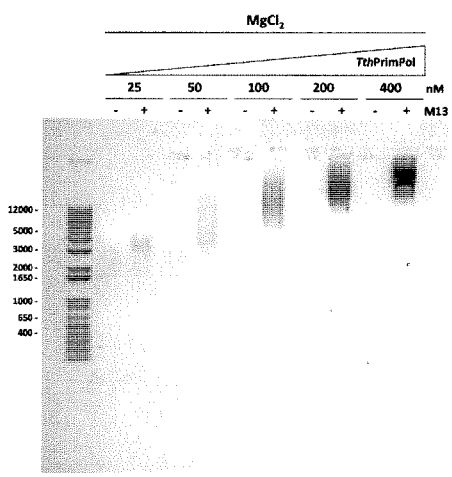
Figure 14B:
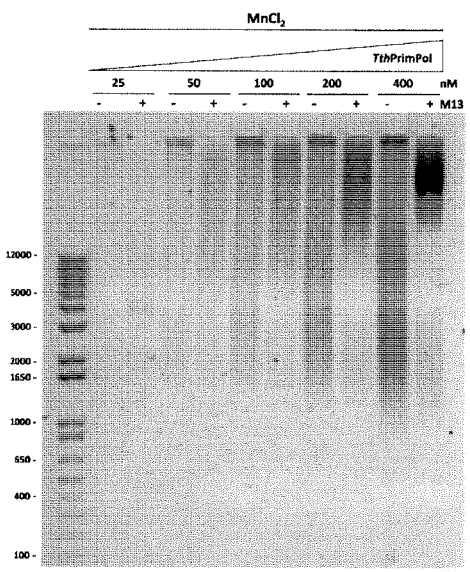
Figure 15:
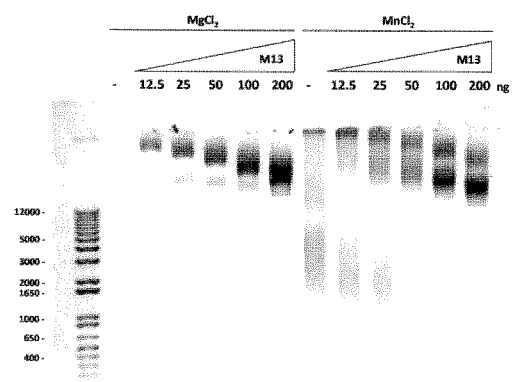
Figure 16A:
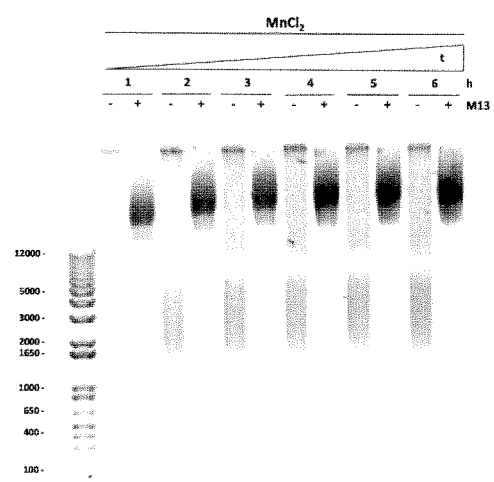
Figure 16B:
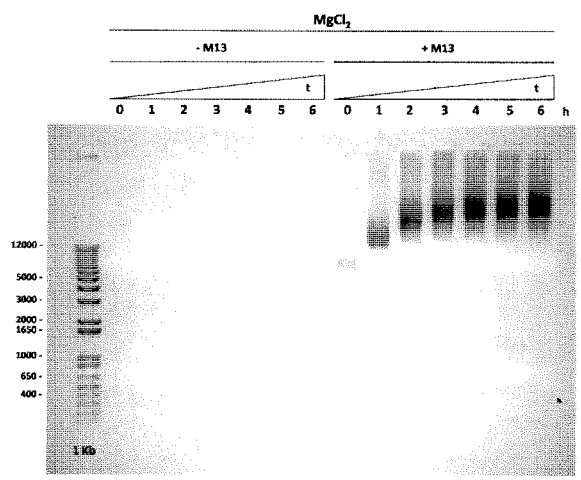
Figure 17:
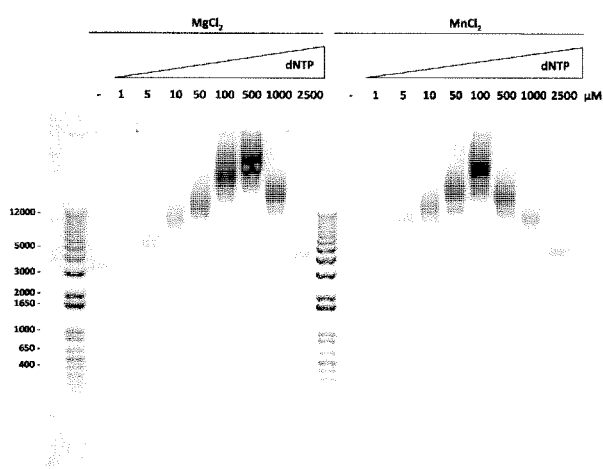
Figure 18:
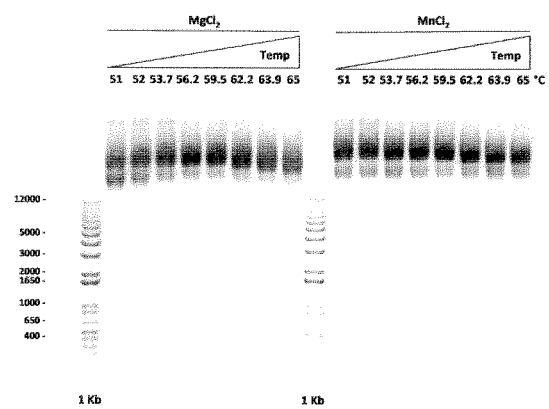

We next analysed the amount of protein necessary to obtain amplification products. As it is shown in FIG. 14 a-b, the yield of the amplification reaction was proportional to the amount of TthPrimPol used in the assay, using either magnesium or manganese as metal cofactors. Likewise, the amount of amplified products depended on the initial amount of template DNA (see FIG. 15). Whereas the reaction time, as shown (FIG. 16 a and b), amplification reached an apparent limit at 4 hours independently of metal cofactor used ($Mn^{2+}$ or $Mg^{2+}$), perhaps due to dNTP deprivation. In addition, the effect of nucleotide concentration was also studied. FIG. 17 shows the amplification products variation in amount and mobility as a function of dNTP concentration. The best dNTP concentration for each metal cofactor ranged from 100 μM when using manganese to 500 μM in the case of magnesium. Higher concentrations seemed to be inhibitory. The amplified products ($Mg^{2+}$ vs. $Mn^{2+}$) had similar mobility and yield considering the effective intervals of dNTP for each metal. Finally, the incubation temperature was analysed to determine the temperatures for each metal cofactor that maximized the amplification yield. As shown (FIG. 18), the optimal temperature range for each metal cofactor was 55-60° C. when using magnesium, and 52-62° C. in the case of manganese.

Example 8

Figure 19:
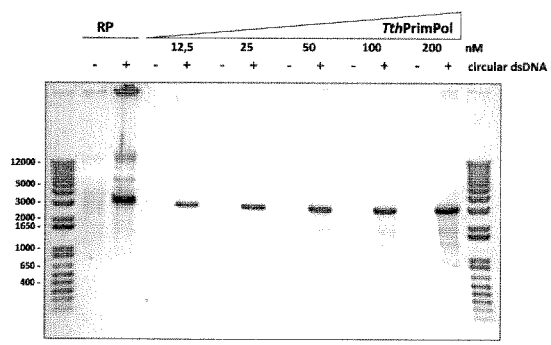
Figure 20:
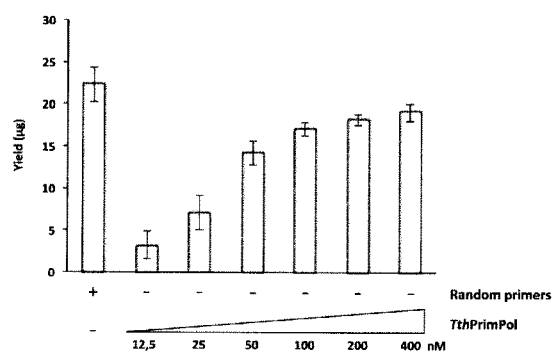

TthPrimPol is Able to Prime DNA for Subsequent Amplification by Phi29 DNA Polymerase Starting from the basis that TthPrimPol is an efficient and versatile DNA primase, we analysed the ability of TthPrimPol to randomly prime circular dsDNA. This primed DNA would then be valid for multiple displacement amplification by Phi29 DNApol. Later on, displaced strands generated by Phi29 DNApol would constitute new substrates for TthPrimPol, where the enzyme could synthesize new primers randomly, thus producing new initiation sites for Phi29 DNApol and reaching the exponential DNA amplification. As shown in FIG. 19, the combination of both enzymes was able to proficiently amplify plasmid DNA, and the amount of amplification products increased in TthPrimPol dose-dependent manner, making unnecessary the addition of random synthetic primers. In order to analyse the ability of TthPrimPol to efficiently prime genomic DNA, the inventors run a series of whole genome amplification experiments. Again, the inventors obtained amplified DNA in a TthPrimPol dose-dependent manner, reaching its maximum at the addition of 400 nM TthPrimPol. No higher amounts tested. These examples clearly demonstrate that TthPrimPol is able to substitute synthetic hexanucleotides in either the amplification of circular DNA as well as in the amplification of linear DNA (FIG. 20).

Example 9

TthPrimPol is a More Efficient Polymerase than HsPrimPol

Figure 22:
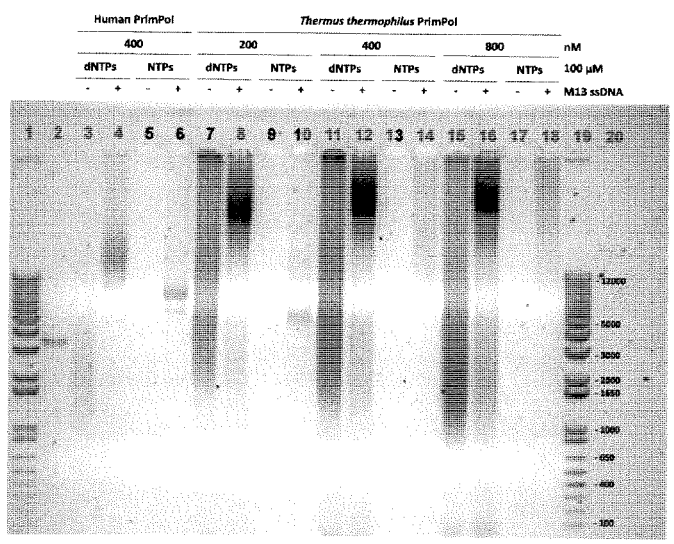

Despite TthPrimPol's thermostability, the enzyme shares most of its basic functionality with the well characterized (seen Garcia Gómez, 2012) HsPrimPol. We therefore wanted to know whether both enzymes are able to amplify DNA, without addition of neither random nor specific primers, in a comparable manner. Therefore, comparable amounts of TthPrimPol and HsPrimPol were used to amplify M13mp18 ssDNA in the absence of primers, but at their respective optimal reaction temperature. In the presence of NTPs, TthPrimPol and HsPrimPol produced comparable amounts of product, But in contrast, in the presence of dNTPs, TthPrimPol acted by far more efficient than the HsPrimPol enzyme, leading to a remarkably greater amount of amplified DNA, compared to HsPrimPol (FIG. 22).

Example 10

TthPrimPol as a Compound of Kits

Especially for the development of kits, which will frequently be stored in laboratories over longer periods of time, stability of compounds is always an important feature. To address this question, the isolated TthPrimPol can be stored over several months in storage buffer at −20° C. Frequently repeated experiments, testing TthPrimPol's primase and polymerase activity as described herein (see for example FIG. 21) will show no significant decline of the measured activity.

Example 11

Use of TthPrimPol as Primase in Conjunction with Different Polymerases

One embodiment of the current invention is the use of TthPrimPol as a primase together with other polymerases for DNA amplification. Currently, whole genome amplification (WGA) is preferably done using Phi29 DNApol and random oligonucleotides (MDA, multiple displacement amplification)(Spits Le Caignec et at 2006; Spits. Le Caignec et al. 2006; Silander and Saarela 2008; Alsmadi, Alkayal et al. 2009). WGA is a kind of strand displacement amplification, performed on linear genomic DNA. Another kind of strand displacement amplification is rolling circle amplification (RCA), as used for the amplification of covalently closed circular DNA. Again, Phi29 DNApol is the preferred enzyme for RCA methods. TthPrimPol can replace oligonucleotides in both, WGA and RCA, amplification methods as shown in FIGS. 19 and 20. Due to its proposed native role as re-initiator of arrested replication forks, TthPrimPol will beneficial be used in a cooperative manner in conventional PCR methods.

Example 12

DNA Labelling

Figure 23:
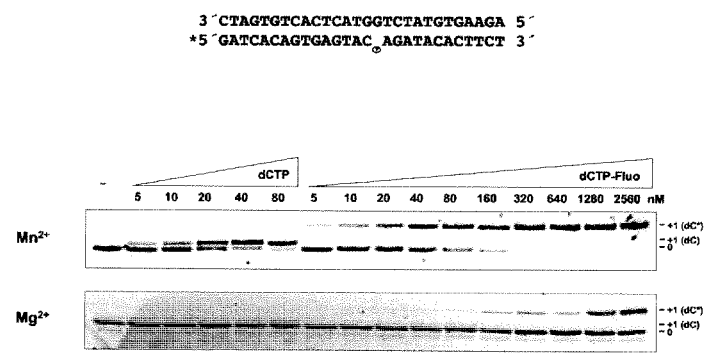

In one embodiment TthPrimPol is used in a method for replicating or amplifying nucleic acid which comprises incorporation of labelled nucleotides into the complementary DNA strand. For example, nucleotides with fluorescent moieties (FIG. 23) or radioactive nucleotides can be used to label DNA molecules for detection in assays. TthPrimPol is well suited for this because of its high processivity, and the high tolerance for nucleotides to be incorporated. Such labelling can also be used for sample preparation for DNA arrays, like for example Affymetrix arrays.

Example 13

Mutating DNA

TthPrimPol can be used to mutate DNA, for example by heavily oxidizing the template strand ad letting TthPrimPol amplify the parental DNA. By the incorporation of different nucleotides (FIGS. 7 and 8) random mutagenesis will be achieved.

Example 14

Amplification of DNA and RNA

TthPrimPol can be used due to its high processivity to amplify DNA, with or without primers, in applications similar to the ones in which Phi29 DNA polymerase is used.

Moreover, TthPrimPol can be used to amplify RNA in its function as a RNA-dependent RNA polymerase. This is especially needed when trying to obtain the expression profile of a single cell or a few cells, for example from neurons in the CNS or from cells in oncological research. So far, RNA amplification protocols relied on procedures with many steps e.g. (Rossner, Hirrlinger et al. 2006; Newrzella, Pahlavan et al. 2007). TthPrimPol based RNA amplification will produce a homogenous, non-biased amplification product. An added advantage is the high temperature during which the amplification can be performed, which would inhibit relevant RNAses, end dissolve secondary structures.

Example 15

Suppression of Unspecific Background DNA

Surprisingly, the inventors found that the combination of both enzymes. TthPrimPol and Phi29 DNA polymerase, do not produce DNA amplification in the absence of externally added template DNA molecules (FIG. 26 a), in any of the incubation times tested (up to 16 hours). In such conditions, TthPrimPol's primase activity seems to depend on the presence of denatured DNA (single strand DNA).

Therefore, in a further embodiment, the combination of TthPrimPol and Phi29 DNA polymerase is used to avoid amplification of contaminating DNA in isothermal MDA amplifications. Such contaminating DNA is often found in difficult to avoid is nucleic acid material that comes with enzyme preparations or reagents.

Example 16

Whole Genome Sequencing of DNA Probes Amplified by a Combination of TthPrimPol and Phi29 Polymerase The cooperative amplification using a combination TthPrimPol and Phi29-pol (Tth/Phi) allows amplifying of smallest amounts of DNA (Example 14), making it an ideal method for the generation of all-purpose DNA probes from limited amounts of template DNA. While conventional MDA introduces a bias, mainly a copy number bias, depending on the composition of the target DNA and the random primers (Alsmadi 2009), we tested if Tth/Phi amplification of DNA allows for a less biased amplification.

Therefore, and in order to determine the quality of Tth/Phi amplified DNA, we sequenced non-amplified yeast (strain BY7471) DNA (NA), amplified (random primed) yeast DNA (RP), and DNA amplified by a Tth/Phi (using varying amounts of TthPrimPol: 100 ng, 200 ng and 400 ng) on a MiSeq (Illumina. USA) sequencing machine.

Assessment of basic quality values was done using the FastX-toolkit (hannonlab.cshLedu/fastx_toolkit), but this revealed no significant difference among all tested samples, thus allowed to conclude that the Tth/Phi amplification method is well suited for the preparation of next generation sequencing (NGS) probes.

In order to discriminate against variations deriving from the preparation of the sequence library, an equal amount (1.4 million) of randomly chosen, high quality (Phred values>20; Ewing B. et al. 1991) paired-end sequence reads (2.8 million single end reads) were used for all further analysis steps.

The software 'CLC Genomic Workbench' Version 7.0 (CLC Bio; Denmark) was used to further analyze the NGS data set. This software is a feature rich integrated software solution for NGS sequence analysis and enables not only to map all reads to a reference genome, but also (based on said mapping) to identify overrepresented and underrepresented genomic regions. Performing such a mapping analysis for all samples, the inventors unexpectedly found that over 90% of all NA (90.48%) and Tth/Phi reads (91.92% and 91.90%) map to the reference, while only 33.92% of the RP reads map to the reference (FIG. 28). This difference between Tth/Phi and RP is also underpinned by a significant difference (p=0.00029) in over- and underrepresented regions on the chromosome level.

In the case of amplified DNA, the total amount of over- and underrepresented regions is a measure for the overall bias introduced by both, the sequencing and the amplification method. In contrast, for the NA sample, the total amount of over- and underrepresented regions only depends on the sequencing method.

The relative difference, if comparing RP to NA and Tth/Phi to NA, is therefore a measure for the bias introduced solely by the amplification method. Accordingly Tth/Phi amplification introduces 17% less bias than RP amplification, demonstrating a clear benefit of Tth/Phi amplification over RP amplification (FIG. 29).

REFERENCES

Alsmadi, O., F. Alkayal, et al. (2009). "Specific and complete human genome amplification with improved yield achieved by phi29 DNA polymerase and a novel primer at elevated temperature." BMC Res Notes 2: 48.
Altschul, S. F., W. Gish, et al. (1990). "Basic local alignment search tool." J Mol Biol 215(3): 403-10.
Aravind, L., D. D. Leipe, et al. (1998). "Toprim—a conserved catalytic domain in type IA and II topoisomerases, DnaG-type primases, OLD family nucleases and RecR proteins." Nucleic Acids Res 26(18): 4205-13.
Bentley, D. R., S. Balasubramanian, et al. (2008). "Accurate whole human genome sequencing using reversible terminator chemistry." Nature 456(7218): 53-9.
Bernad, A., L. Blanco, et al. (1989). "A conserved 3'-5' exonuclease active site in prokaryotic and eukayotic DNA polymerases." Cell 59(1): 219-28.
Berquist, B. R. and D. M. Wilson, 3rd (2012) "Pathways for repairing and tolerating the spectrum of oxidative DNA lesions." Cancer Lett 327(1-2): 61-72.
Blainey et. al (2011) Nucleic Acids Research Vol. 39, No. 4
Branton, D., D. W. Deamer, et al. (2008). "The potential and challenges of nanopore sequencing." Nat Biotechnol 26(10): 1146-53.
Butler, T. Z., M. Pavlenok, et al. (2008). "Single-molecule DNA detection with an engineered MspA protein nanopore." Proc Natl Acad Sci USA 105(52): 20647-52.
Cavanaugh, N. A. and R. D. Kuchta (2009). "Initiation of new DNA strands by the herpes simplex virus-1 primase-helicase complex and either herpes DNA polymerase or human DNA polymerase alpha." J Biol Chem 284(3): 1523-32.
Champlot S, Berthelet C, Pruvost M. Bennett E A, Grange T, et al. (2010) "An Efficient Multistrategy DNA Decontamination Procedure of PCR Reagents for Hypersensitive PCR Applications". PLoS ONE 5(9)
Chemnitz Galal, W., M. Pan, et al. (2012) "Characterization of DNA primase complex isolated from the archaeon, Thermococcus kodakaraensis." J Biol Chem 287(20): 16209-19.
Clarke, J., H. C. Wu, et al. (2009). "Continuous base identification for single-molecule nanopore DNA sequencing." Nat Nanotechnol 4(4): 265-70.
Corless et al., JOURNAL OF CLINICAL MICROBIOLOGY. May 2000, p. 1747-1752 Derrington, I. M., T. Z. Butler, et al. (2010) "Nanopore DNA sequencing with MspA." Proc Natl Acad Sci USA 107(37): 16060-5.
Eid, J., A. Fehr, et al. (2009). "Real-time DNA sequencing from single polymerase molecules." Science 323(5910): 133-8.
Ewing B, Hillier L, Wendl M C, Green P (1998). "Base-calling of automated sequencer traces using phred. I. Accuracy assessment". Genome Res. 8 (3): 175-185
Ewing B, Hillier L, Wendl M C, Green P (1998). "Base-calling of automated sequencer traces using phred. I. Accuracy assessment". Genome Res. 8 (3): 16-194
Frick, D. N. and C. C. Richardson (2001). "DNA primases." Annu Rev Bichem 70: 39-80.
García Gómez, S. I., M. I. Martinez Jiménez, et al. (2012). PrimPol a two in one enzyme: primase and bypass polymerase. From Single Molecules to System Biology. Sevilla, IUBMB FEBS.
Gerard, G. F., D. K. Fox, et al. (1997). "Reverse transcriptase. The use of cloned Moloney murine leukemia virus reverse transcriptase to synthesize DNA from RNA." Mol Biotechnol 8(1): 61-77.
Guo, J., N. Xu, et al. (2008). "Four-color DNA sequencing with 3â€-O-modified nucleotide reversible terminators and chemically cleavable fluorescent dideoxynucleotides." Proceedings of the National Academy of Sciences 105(27): 9145-9150.
Han et al. (2012) BMC Genomics. 13:217)
Hein et al., Journal of Microbiological Methods 71 (2007) 336-339
Hinz, H. J., C. Steif, et al. (1993). "Fundamentals of protein stability." Pure & Appl. Chem. 65(5): 5.
Holmes, A. M., E. Cheriathundam, et at (1985). "Initiation of DNA synthesis by the calf thymus DNA polymerase-primase complex." J Biol Chem 260(19): 10840-6.
Hosono et al. (2003) Genome Res 13:954-964)
Ilyina, T. V. and E. V. Koonin (1992). "Conserved sequence motifs in the initiator proteins for rolling circle DNA replication encoded by diverse replicons from eubacteria, eucaryotes and archaeabacteria." Nucleic Acids Res 20(13): 3279-85.
Iyer, L. M., E. V. Koonin, et al. (2005). "Origin and evolution of the archaeo-cukaryotic primase superfamily and related palm-domain proteins: structural insights and new members." Nucleic Acid Res 33(12): 3875-96.
Jetha, N. N., M. Wiggin, et al. (2009). "Forming an alpha-hemolysin nanopore for single-molecule analysis." Method Mol Biol 544: 113-27.
Ju, J., D. H. Kim, et al. (2006). "Four-color DNA sequencing by synthesis using cleavable fluorescent nucleotide reversible terminators." Proceedings of the National Academy of Sciences 103(52): 19635-19640.
Kim. Y. H., A. H. Berry, et al. (2001). "Comparing the effect on protein stability of methionine oxidation versus mutagenesis: steps toward engineering oxidative resistance in proteins." Protein Eng 14(5): 343-7.
Kornberg A. and T. Baker (1991). DNA Replication, 2nd edn. W.H. Freeman & Company, NY.
Lage et al., (2003) Genome Res 3:294-307).
Lao-Sirieix, S. H. and S. D. Bell (2004). "The heterodimeric primase of the hyperthermophilic archaeon Sulfolobus solfataricus possesses DNA and RNA primase, polymerase and 3'-terminal nucleotidyl transferase activities." J Mol Biol 344(5): 1251-63.
La-Sirieix. S. H., L. Pellegrini, et al. (2005). "The promiscuous primase." Trends Genet 21(10): 561-72.
Lieberman, K. R., G. M. Cherf, et al. (2010) "Processive replication of single DNA molecules in a nanopore catalyzed by phi29 DNA polymerase." J Am Chem Soc 132(50): 17961-72.
Lipps. G. (2004). "The replication protein of the Sulfolobus islandicus plasmid pRN1." Biochem Soc Trans 32(Pt 2): 240-4.
Lipps, G., S. Rother, et al. (2003). "A novel type of replicative enzyme harbouring ATPase, primase and DNA polymerase activity." EMBO J 22(10): 2516-25.

Lipps G., A. O. Weinzierl, et al. (2004). "Structure of a bifunctional DNA primase-polymerase." *Nat Struct Mol Biol* 11(2): 157-62.

Litosh, V. A., W. Wu, et at (2011). "Improved nucleotide selectivity and termination of 3'-OH unblocked reversible terminators by molecular tuning of 2-nitrobenzyl alkylated HOMedU triphosphates." *Nucleic Acid Res* 39(6): e39.

Lodish, H. B., A.; Zipuraki, S. L., Masudaira, P.; Baltimore. D.; Darnell, E. J. (1999). *Molecular Cell Biology*. W.H. Freemann & Co., NY.

Macaulay I C, Voet T (2014) "Single Cell Genomics: Advances and Future Perspectives". *PLoS Genet* 10(1).

Maglia, G., M. R. Restrepo, et al. (2008). "Enhanced translocation of single DNA molecules through alpha-hemolysin nanopores by manipulation of internal charge." *Proc Natl Acad Sci USA* 105(50): 19720-5.

Manrao, E. A., I. M. Derrington, et al. (2012) "Reading DNA at single-nucleotide resolution with a mutant MspA nanopore and phi29 DNA polymerase." *Nat Biotechnol* 30(4): 349-53.

Manrao, E. A., I. M. Derrington, et al. (2011) "Nucleotide discrimination with DNA immobilized in the MspA nanopore." *PLoS One* 6(10): e25723.

Maxam, A. M. and W. Gilbert (1977). "A new method for sequencing DNA." *Proc Natl Acad Sci USA* 74(2): 560-4.

Metzker, M. L. (2009). "Sequencing technologies—the next generation." *Nat Rev Genet* 11(1): 31-46.

Moser, M. J., R. A. DiFrancesco, et al. (2012). "Thermostable DNA polymerase from a viral metagenome is a potent RT-PCR enzyme." *PLoS One* 7(6): e38371.

Myers, T. W. and D. H. Gelfand (1991). "Reverse transcription and DNA amplification by a *Thermus thermophilus* DNA polymerase." *Biochemistry* 30(31): 7661-6

Newrzella, D., P. S. Pahlavan, et al. (2007). "The functional genome of CA1 and CA3 neurons under native conditions and in response to ischemia." *BMC Genomics* 8: 370.

Noirot-Gros, M. F. and S. D. Ehrlich (1996). "Change of a catalytic reaction carried out by a DNA replication protein." *Science* 274(5288): 777-80.

Paez et al. (2004) Nucleic Acids Res 32:e71.

Parker, W. B. and Y. C. Cheng (1987). "Inhibition of DNA primase by nucleoside triphosphates and their arabinofuranosyl analogs." *Mol Pharmacol* 31(2): 146-51.

Pavlenok, M., I. M. Derrington, at al. (2012) "MspA nanopores from subunit dimers." *PLoS One* 7(6): e38726.

Pinard et al. (2006) *BMC Genomics* 7:216.

Pugh et al. (200) *Nucleic Acids Research* Vol. 36, No. 13.

Raghunathan et al. (2005) Appl Environ Microbiol 71:3342-3347.

Ronaghi, M., S. Karamohamed, et at (1996). "Real-time DNA sequencing using detection of pyrophosphate release." *Anal Biochem* 242(1): 84-9.

Ronaghi, M., M. Uhlen, et al. (1998). "A sequencing method based on real-time pyrophosphate." *Science* 281(5375): 363, 365.

S Rossner, M. J., J. Hirrlinger, et al. (2006). "Global transcriptome analysis of genetically identified neurons in the adult cortex." *J Neurosci* 24(39): 9956-66.

Sales, M. (1991). "Protein-priming of DNA replication." *Annu Rev Biochem* 60: 39-71.

Sam, L. T., D. Lipson, et at (2011) "A comparison of single molecule and amplification based sequencing of cancer transcriptomes." *PLoS One* 6(3): e17305.

Sanchez-Berrondo, J., P. Mesa, et al. (2011) "Molecular architecture of a multifunctional MCM complex." *Nucleic Acids Res* 40(3): 1366-80.

Sanger. F. and A. R. Coulson (1978). "The use of thin acrylamide gels for DNA sequencing." *FEBS Lett* 87(1): 107-10.

Sanger, F., S. Nicklen, et al. (1977). "DNA sequencing with chain-terminating inhibitors." *Proc Natl Acad Sci USA* 74(12): 5463-7.

Schoenfeld, T., M. Liles, et al. (2009). "Functional viral metagenomics and the next generation of molecular tools." *Trends Microbiol* 18(1): 20-9.

Schoenfeld, T., M. Patterson, et al. (2008). "Assembly of viral metagenomes from yellowstone hot springs." *Appl Environ Microbiol* 74(13): 4164-74.

Silander, K. and J. Saarela (2008). "Whole genome amplification with Phi29 DNA polymerase to enable genetic or genomic analysis of samples of low DNA yield." *Methods Mol Biol* 439: 1-18.

Simpson, R. J. (2005). "Stabilization of proteins for storage." *Cold Spring Harb Protoc* 2010(5): pdb top79.

Spits, C., C. Le Caignec, et al. (2006). "Optimization and evaluation of single-cell whole-genome multiple displacement amplification." *Hum. Mutat* 27(5): 496-503.

Spits, C., C. Le Caignec, et al. (2006). "Whole-genome multiple displacement amplification from single cells." *Nat Protoc* 1(4): 1965-70.

Thompson, J. F. and P. M. Milos (2011) "The properties and applications of single-molecule DNA sequencing." *Genome Biol* 12(2): 217.

Turcatti, G., A. Romieu, et al. (2008). "A new class of cleavable fluorescent nucleotides: synthesis and optimization as reversible terminators for DNA sequencing by synthesis." *Nucleic Acids Research* 36(4): e25.

Wendell, D., P. Jing, et al. (2009). "Translocation of double-stranded DNA through membrane-adapted phi29 motor protein nanopores." *Nat Nanotechnol* 4(11): 765-72.

Woyke T, Sczyrbe A, Lee J. Rinke C. Tighe D, et al. (2011) "Decontamination of MDA Reagents for Single Cell Whole Genome Amplification". *PLoS One* 6(10)

Wu, W., B. P. Stupi, et al. (2007). "Termination of DNA synthesis by N6-alkylated, not 3'-O-akylated, photocleavable 2'-deoxyadenosine tripliosphiates." *Nucleic Acids Res* 35(19): 6339-49.

Zhang L, Cui X. Schmitt K. Hubert R, Navidi W. et al. (1992). "Whole genome amplification from a single cell: implications for genetic analysis". *Proc Natl Acad Sci USA* 39: 5847-5851

The invention further relates to the following items 1 to 23:

1. A method for replicating, amplifying or sequencing of nucleic acids comprising the following steps
   a) providing
      i. a polymerase, or
      ii. a polymerase conjugate,
         wherein the polymerase, or the polymerase moiety of the polymerase conjugate having a sequence that is at least 70% identical to SEQ ID NO: 1 and further comprises polymerase and primase activity, and
   b) providing a template nucleic acid, and
   c) providing nucleotides and/or nucleotide derivatives for incorporation in a complementary strand of nucleic acids, and
   d) providing a suitable buffer, and
   e) optionally providing one or e primers, and
   f) contacting the materials of steps a-e for a suitable amount of time, optionally at high temperature, preferably at temperatures over 40° C., most preferred over 50° C.

2. A method of item 1, wherein the polymerase of a) i), or the polymerase moiety of the polymerase conjugate a) ii) having a sequence that is at least 80% identical to SEQ ID NO: 1
3. A method of item 1, wherein the polymerase of a) i), or the polymerase moiety of the polymerase conjugate of a) ii) having a sequence that is at least 90% identical to SEQ ID NO: 1
4. A method of item 1, wherein the polymerase of a) i) or the polymerase moiety of the polymerase conjugate of a) ii) having the sequence of SEQ ID NO: 1
5. A method according to any one of items 1-4, wherein the nucleic acid of step b) is damaged.
6. A method according to item 5, wherein the damaged nucleic acid is characterized by:
   a) comprising single strand or double strand breaches, and/or
   b) comprising chemically modified nucleotides, preferably selected from the group of oxidized nucleotides and/or deaminated nucleotides, most preferably selected from the group consisting of 7,8-dihydro-8-oxoadenine, 7,8-dihydro-8-oxoguanine, thymine glycol, 5-hydroxycytisine 5-hydroxyuracil and/or
   c) derived from formaldehyde or para-formaldehyde embedded tissue.
7. A method according to any one of items 1-6, wherein at least one species of nucleotide derivatives of step c) is a chemically modified nucleotide.
8. A method of item 7, wherein the nucleotide derivative of step c) comprises at least one species of nucleotide derivatives selected from the group consisting of:
   a) oxidized nucleotide derivative, and/or
   b) deaminated nucleotides,
   c) derivatives comprising at least one sterically demanding side group.
9. A method according to any one of items 1-8, wherein the template nucleic acid of step b) derives from less than 100 cells, preferably from a single cell.
10. A method according to any one of items 1-9, wherein no primer is provided for step e)
11. A method according to any one of items 1-10, wherein the nucleic acid of step b) is deoxyribonucleic acid (DNA).
12. A method according to any one of items 1-10, wherein the nucleic acid of step b) is ribonucleic acid (RNA).
13. A method of item 12, comprising reverse transcription of RNA.
14. A method according to any one of item 1-12, comprising a second polymerase.
15. A method of item 14, wherein said second polymerase is selected from the group consisting of prokaryotic family A polymerases, prokaryotic family B polymerases.
16. A method of item 14, wherein said second polymerase is selected from the group consisting of Taq polymerase, Tth polymeras, Pfu polymerase, Vent polymerase.
17. A method of item 14, wherein said second polymerase is a Phi29 type DNA polymerase or a conjugate thereof
18. A polymerase or polymerase conjugate as defined in any one of the items 1-4 for use in a method according to any one of the items 1-17.
19. A method for detecting modifications, in particular for detecting products of oxidation processes, in a DNA template, comprising the steps
   a) performing multiple sequence reads according to any one of the items 1-4, and
   b) calculating the relative percentage of incorporated nucleotides for each nucleotide position over all sequence reads of step a, and
   c) correlating the overall percentage of incorporated nucleotides with the original nature of the DNA modification in the template.
20. A method for random mutagenesis, comprising the steps
   a) contacting a nucleic acid with an oxidative compound, whereby said contacting leads to the oxidation of bases of the nucleic acid, and
   b) replicating the oxygenated nucleic acid with a polymerase or a polymerase conjugate as defined in anyone of the items 1-4.
21. A kit for amplifying a DNA molecule, that is storable under suitable conditions for more than 20 months comprising:
   a) a first container comprising a polymerase according to items 1-4
   b) a second container comprising one or more deoxyribonucleoside triphosphates
22. A kit for amplifying a RNA molecule, that is storable under suitable conditions for more than 20 months, comprising:
   a) a first container comprising a polymerase according to items 1-4
   b) a second container comprising one or more ribonucleoside triphosphates
23. A kit for sequencing a nucleic acid molecule, that is storable under suitable conditions for more than 20 months, comprising:
   a) a first container comprising a polymerase according to items 1-4
   b) a second container comprising one or more dideoxyribonucleoside triphosphates
   c) a third container comprising one or more deoxyribonucleoside triphosphates

What is claimed is:

1. A method for replicating, amplifying or sequencing of DNA in the absence of a primer comprising the following steps
   a) providing
      i) a protein that has both polymerase and primase activity, and has a sequence that is at least 80% identical to SEQ ID NO: 1, or
      ii) a conjugate comprising a protein moiety that has both polymerase and primase activity, wherein the protein moiety of the conjugate has a sequence that is at least 80% identical to SEQ ID NO: 1,
   b) providing a template nucleic acid,
   c) providing nucleotides and/or nucleotide derivatives for incorporation in a complementary strand of nucleic acids,
   d) providing a suitable buffer,
   e) providing a second polymerase, and
   f) contacting the materials of steps a-e in the absence of a primer and without the presence of a protein having primase activity other than the protein or conjugate provided in step (a) for a suitable amount of time to replicate, amplify or sequence the template nucleic acid.

2. The method of claim 1, wherein the second polymerase provided in step e) is selected from the group consisting of prokaryotic family A polymerases and prokaryotic family B polymerases.

3. The method according to claim 2, wherein the second polymerase is a thermostable polymerase selected from the group consisting of Taq polymerase, Tth polymerase, Pfu polymerase, and Vent polymerase.

4. The method of claim 1, wherein the second polymerase provided in step e) is a Phi29 type DNA polymerase or a conjugate thereof.

5. The method according to claim 1, wherein the protein of a) i) has a sequence that is at least 95% identical to SEQ ID NO: 1, or the protein moiety of the conjugate of a) ii) has a sequence that is at least 95% identical to SEQ ID NO: 1.

6. The method according to claim 1, wherein the protein of a) i) has a sequence that is at least 90% identical to SEQ ID NO: 1, or the protein moiety of the conjugate of a) ii) has a sequence that is at least 90% identical to SEQ ID NO: 1.

7. The method according to claim 1, wherein the protein of a) i) has the sequence set forth as SEQ ID NO: 1, or the protein moiety of the conjugate of a) ii) has the sequence set forth as SEQ ID NO: 1.

8. The method according to claim 1, wherein step (b) comprises providing a template nucleic acid which is damaged.

9. The method according to claim 8, wherein the damaged template nucleic acid is characterized by:
- a) the presence of at least one single strand or double strand breach, and/or
- b) the presence of at least one chemically modified nucleotide, and/or
- c) being derived from formaldehyde or para-formaldehyde embedded tissue.

10. The method according to claim 1, wherein step c) comprises providing nucleotide derivatives for incorporation in a complementary strand of nucleic acids, and at least one species of the nucleotide derivatives is a chemically modified nucleotide.

11. The method of claim 1, wherein step c) comprises providing nucleotide derivatives for incorporation in a complementary strand of nucleic acids, and at least one species of the nucleotide derivatives of step c) is selected from the group consisting of:
- a) oxidized nucleotide derivative,
- b) deaminated nucleotides, and
- c) derivatives comprising at least one sterically demanding side group.

12. The method according to claim 1, wherein the template nucleic acid of step b) derives from less than 100 cells, preferably from a single cell.

13. The method according to claim 1, wherein the amplification of contaminant DNA is suppressed.

14. The method according to claim 9, wherein a single strand breach is present in the damaged template nucleic acid.

15. The method according to claim 9, wherein at least one chemically modified nucleotide is present in the damaged template nucleic acid, and the chemically modified nucleotide is selected from the group consisting of 7,8-dihydro-8-oxoadenine, 7,8-dihydro-8-oxoguanine, thymine glycol, 5-hydroxycytosine and 5-hydroxyuracil.

16. The method according to claim 10, wherein the chemically modified nucleotide is selected from the group consisting of 7,8-dihydro-8-oxoadenine, 7,8-dihydro-8-oxoguanine, thymine glycol, 5-hydroxycytosine and 5-hydroxyuracil.

17. The method according to claim 8, wherein step c) comprises providing nucleotide derivatives for incorporation in a complementary strand of nucleic acids, and at least one species of the nucleotide derivatives is a chemically modified nucleotide.

18. The method according to claim 17, wherein the chemically modified nucleotide is selected from the group consisting of 7,8-dihydro-8-oxoadenine, 7,8-dihydro-8-oxoguanine, thymine glycol, 5-hydroxycytosine and 5-hydroxyuracil.

19. The method according to claim 1, wherein the polymerase or the polymerase moiety of the polymerase conjugate is capable of replicating, amplifying or sequencing DNA when a mix of nucleotides and nucleotides derivatives is provided in step c).

* * * * *